United States Patent [19]

Nobuyoshi et al.

[11] Patent Number: 5,403,339

[45] Date of Patent: Apr. 4, 1995

[54] BLOOD VESSEL DILATOR

[75] Inventors: Masakiyo Nobuyoshi, Kitakyushu; Hirokazu Itoh; Kyuta Sagae, both of Nakai, all of Japan

[73] Assignee: Terumo Kabushiki Kaisha, Tokyo, Japan

[21] Appl. No.: 901,761

[22] Filed: Jun. 19, 1992

[30] Foreign Application Priority Data

Jun. 21, 1991 [JP] Japan .................... 3-177228

[51] Int. Cl.⁶ .......................................... A61M 29/00
[52] U.S. Cl. ..................................... 606/194; 604/96
[58] Field of Search ...................... 606/191, 194, 195; 604/95–102

[56] References Cited

U.S. PATENT DOCUMENTS

| | | | |
|---|---|---|---|
| 3,703,899 | 11/1972 | Calinog | 604/170 |
| 4,323,071 | 4/1982 | Simpson et al. | |
| 4,362,150 | 12/1982 | Lombardi, Jr. et al. | 604/99 |
| 4,616,653 | 10/1986 | Samson et al. | |
| 4,665,925 | 5/1987 | Millar | |
| 4,723,936 | 2/1988 | Buchbinder et al. | 604/95 |
| 4,771,778 | 9/1988 | Mar | |
| 4,917,666 | 4/1990 | Solar et al. | 604/95 |
| 4,931,036 | 6/1990 | Kanai et al. | 604/99 |
| 4,932,959 | 6/1990 | Horzewski et al. | 604/96 |
| 4,998,923 | 3/1991 | Samson et al. | 604/95 |
| 5,032,113 | 7/1991 | Burns | |
| 5,246,420 | 9/1993 | Kraus et al. | 604/95 |

FOREIGN PATENT DOCUMENTS

| | | |
|---|---|---|
| 0231601A3 | 8/1987 | European Pat. Off. |
| 0351687A3 | 1/1990 | European Pat. Off. |
| 0368523A3 | 5/1990 | European Pat. Off. |
| WO91/13649 | 9/1991 | WIPO |
| WO92/08511 | 5/1992 | WIPO |

Primary Examiner—Stephen C. Pellegrino
Assistant Examiner—William Lewis
Attorney, Agent, or Firm—Frishauf, Holtz, Goodman & Woodward

[57] ABSTRACT

A blood vessel dilator so thin in outside dameter as the "on the wire" type catheter retaining a sufficiently wide liquid lumen and highly manipulatable at branched parts of blood vessels by a separately turnable guide wire and hence readily inserted even into narrow peripheral blood vessels.

This blood vessel dilator comprises a main tube; a distal-end tube put in the distal end portion of the main tube with its front end portion protruding out of the distal end of the main tube; a dilatation element with its front end portion connected to the front end portion of the distal-end tube and its rear end portion to the distal end portion of the main tube; a resilient core member put through the inside of the main tube and distal-end tube; a leading guide provided at the distal end portion of the resilient core member; a main-tube hub connected to the proximal end of the main tube; and a core-member hub connected to the proximal end of the resilient core member and secured to the main-tube hub turnably with respect to the main tube.

36 Claims, 12 Drawing Sheets

BLOOD VESSEL DILATOR

FIELD OF THE INVENTION

The present invention relates to an instrument for treating stenosis by dilating stenotic lesions in blood vessels and thereby ameliorating the blood flow in the peripheral side of them.

BACKGROUND OF THE INVENTION

Percutaneous Transluminal Coronary Angioplasty (PTCA), an operation which widens the lumen of narrowed parts in blood vessels to ameliorate the blood flow using a catheter with a dilatation element, is practiced as a method of treating stenosis. Catheters with a dilatation element, such as those of the so called "over the wire" type, as disclosed in the specification of U.S. Pat. No. 4,323,071, which are guided over a guide wire passed freely through their interior opening, are used for PTCA. In recent years, however, a need of low-profile catheters is increasing for treating stenosis in more peripheral side blood vessels. But the conventional catheters, for its structure, cannot be made sufficiently lowprofile to pass through such narrow stenotic lesions and cannot cope with this need. Then, the catheter of the so called "on the wire" type, whose dilatation element is directory attached on the guide wire, as disclosed in the specification of U.S. Pat. No. 4,77,778, was devised and is becoming able to treat such difficult cases for its structural advantage that it can be made very lowprofile.

Though the "on the wire" type catheter as disclosed in U.S. Pat. No. 4,771,778 has become able to pass through stenotic lesions in narrow vessels that conventional catheters cannot pass through, it has problems of its own. Since its dilatation element is directly attached on the guide wire, turn of the guide wire can twist and damage the dilatation element. Therefore, the very function of the guide wire, that is, to be turned to enter into a desired vessel, is considerably restricted. Thus, the manipulatability of this type of catheter is lower than that of the conventional "over the wire" type catheters, and it is sometimes difficult to enter the guide wire into a aimed branch vessel.

On the other hand, the catheter disclosed by U.S. Pat. No. 4,616,653 has the dilatation element attached on the catheter body and the guide wire housed in the catheter body as in the conventional "over the wire" type catheter, and its guide wire can be turned freely. However, this type of catheter has a disadvantage that it cannot not be made so thin as the "on the wire" type catheter. Further, since this type of catheter has two lumens, one for passing the guide wire and another for injecting a dilatation liquid into the dilatation element, the liquid lumen cannot be made sufficiently wide and liquid injection is difficult if the catheter body is made very thin as required; on the other hand, the catheter body cannot be made sufficiently thin if the liquid lumen is made so wide so to facilitate liquid injection, though the manipulatability of this type of catheter is very high.

The object of the present invention is to provide a blood vessel dilator which is so thin in outside diameter as the "on the wire" type catheter retaining a sufficiently wide liquid lumen and is highly manipulatable at branched parts of blood vessels by a separately turnably guide wire and hence can be readily inserted even into narrow peripheral blood vessels, in order to solve the above problems of the prior art.

SUMMARY OF THE INVENTION

The above objects is attained by the blood vessel dilator of the present invention as below.

The blood vessel dilator of the present invention comprises a main tube having a lumen; a distal-end tube put in the distal end portion of a main tube with its front end portion protruding out of the distal end of the main tube; a dilatation element with its front end portion connected to the front end portion of the distal-end tube and its rear end portion to the distal end portion of the main tube and inflatable and contractible or foldable when deflated; a resilient core member put through the inside of the main tube and the distal-end tube; a leading guide provided at a distal end portion of the resilient core member; a main-tube hub connected to a proximal end of the main tube; a core-member hub connected to the proximal end of the resilient core member and secured to the main-tube hub turnably with respect to the main tube; an opening communicating with the lumen in the main tube and serving as a port: and the distal-end tube being connected to a distal end of the main tube without blocking the communication of the lumen in the main tube and the inside of the dilatation element, and the distal-end tube having a contact portion whose an inside diameter is substantially equal to or slightly larger than the diameter of the resilient core member partially or over its entire length so as to support the resilient core member turnably and liquid-tight.

The another blood vessel dilator of the present invention comprises a main tube having a lumen; a distal-end tube put in the distal end portion of the main tube with its front end portion protruding out of a distal end of the main tube; a dilatation element with its front end portion connected to a front end portion of the distal-end tube and its rear end portion to a distal end portion of the main tube and inflatable and contractible or foldable when deflated; a resilient core member put through the inside of the main tube and the distal-end tube; a leading guide provided at a distal end portion of the resilient core member; a main-tube hub connected to a proximal end of the main tube and having an opening communicating with the lumen inside the main tube and serving as a port; a core-member hub connected to a proximal end of the resilient core member and secured to the main-tube hub turnably: and the distal-end tube being connected to the distal end of the main tube without blocking the communication of the lumen in the main tube and an inside of the dilatation element, and the distal-end tube having a contact portion whose an inside diameter is so formed substantially equal to or slightly larger than the diameter of the resilient core member partially or over its entire length so as to support the resilient core member turnably and liquid-tight.

The another blood vessel dilator of the present invention comprises a main tube having a smaller-diameter distal end portion and a larger-diameter proximal major portion; a dilatation element with its front end portion connected to the front end portion of the main tube with a smaller diameter and its rear end portion to the major portion of the main tube with a large diameter; a resilient core member put through the inside of the main tube and distal-end tube; a leading guide provided at the distal end portion of the resilient core member; a lumen formed between the proximal major portion of the main tube and the resilient core member; a bore provided in the distal end of the proximal major portion of the main tube for communicating the lumen and the inside of the dilatation element with each other; an opening communicating with the lumen in the main tube and serving as a port; a main-tube hub connected to the proximal end of the main tube and having a bore communicating with the lumen inside the main tube; and a core-member hub connected to the proximal end of the resilient core member, secured to the main-tube hub turnably: and further said smaller-diameter distal end portion of the main tube has a substantially equal to or slightly larger diameter than the diameter of the resilient core member so as to support the resilient core member turnably and liquid-tight.

DETAILED DESCRIPTION OF THE PREFERRED EMBODIMENTS

Figure 1:
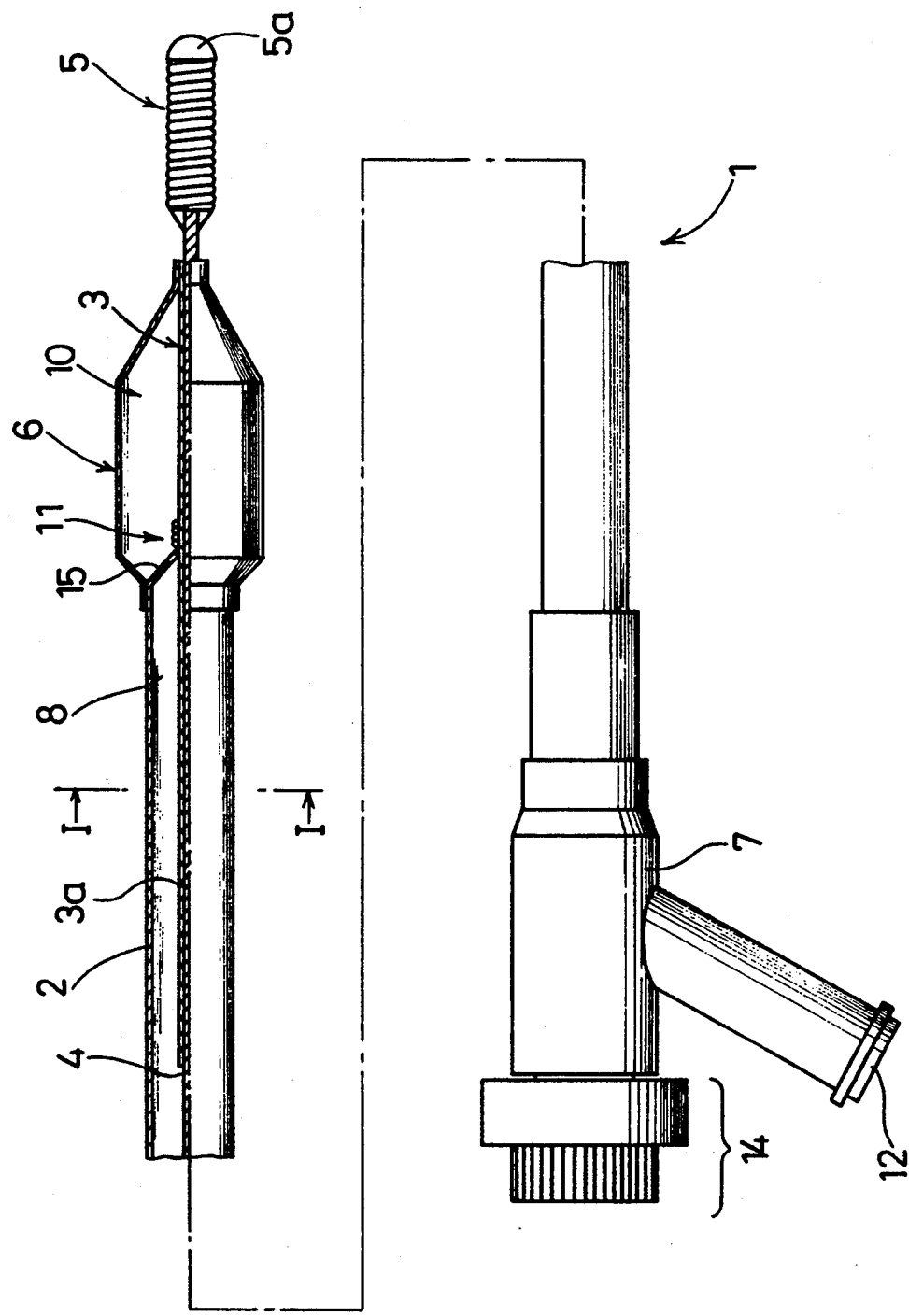
FIG. 1 is a cross-sectional view of a part of an embodiment of the blood vessel dilator according to the present invention.

The blood vessel dilator of the present invention is described below using the embodiments shown in the drawings.

The blood vessel dilator of the present invention 1 comprises a main tube 2 having a lumen 8; a distal-end tube 3 inserted in the distal end portion of the main tube 2 with its front end portion extending out of the distal end of the main tube 2; a dilatation element 6 with its front end portion attached to the front end portion of the distal-end tube 3 and its rear end portion to the distal end portion of the main tube 2; a resilient core member 4 extending through the inside of the main tube 2 and the distal-end tube 3; a leading quid 5 formed at the distal end portion of the resilient core member 4; a main-tube hub 7 attached to the proximal end of the main tube 2 and having an opening which communicates with the lumen 8 formed inside the main tube 2; and a core-member hub 14 attached to the proximal end of the resilient core member 4 and retaining the core member rotatably, allowing it to be turned by hand. The distal end of the main tube 2 is connected with the distal-end tube 3 maintaining the communication between the lumen 8 in the main tube 2 and the inside of the dilatation element 6. The distal-end tube 3 has an extended contact portion 3a whose an inside diameter is substantially equal to or slightly larger than the diameter of the corresponding portion of the resilient core member 4 so as to support the resilient core member turnably and liquid-tight.

Since, in the blood vessel dilator of the present invention, the resilient core member 4 can be turned freely with respect to the main tube 2 and distal-end tube 2, the guiding part 5 at the distal end of the resilient core member 4 is easy to manipulate to insert it into a target location of a blood vessel. Moreover, since the distal-end tube 3 does not extend up to the proximal end of the main tube 2, a larger sectional area is left for the lumen 8 which serves as the passage for injecting a dilatation liquid into the dilatation element, which makes the injection of a dilatation element and hence the dilation of stenotic lesions easier.

The construction of this blood vessel dilator is more specifically described below using the embodiment shown in FIG. 1, which is a diagrammatic sectional view of the distal end portion of an embodiment of the blood vessel dilator according to the present invention.

The blood vessel dilator of this embodiment 1 comprises a main tube 2, a distal-end tube 3, a resilient core member 4, a dilatation element 6, a main tube hub 7 and a core-member hub 14 as described above.

The main tube 2 supports the distal-end tube 3 coaxially in it. Its distal end is situated a little behind the front end of the distal-end tube 3, and its proximal end is extended long behind the rear end of the distal-end tube 3.

The main tube 2 is a tube with a certain amount of flexibility, formed of a flexible plastic or an elastic metal. It may also be formed by connecting a distal portion formed of a flexible plastic and a proximal portion of an high-elasticity metal. Synthetic resins with a good flexibility, such as thermoplastic resins [polyolefin (polyethylene, polypropylene, ethylene-propylene copolymer, ethylene-vinylacetate copolymer, a blend of polypropylene and polybutene, for example), polyvinyl chloride, polyamide elastomer and polyurethane] and polyimide, can be used to form the main tube 2. Polyolefin and polyimide are preferable.

The main tube 2 formed of such materials has a length in the range of 300 to 2000 mm, preferably 500 to 1600 mm; an outer diameter in the range of 0.3 to 1.5 mm, preferably 0.4 to 1.2 mm; and a wall thickness in the range of 30 to 200 $\mu$m, preferably 50 to 150 $\mu$m. It is also desirable that the main tube 2 has a length two times or more greater than that of the distal-end tube 3, in other words the distal-end tube 3 is less than half the length of the main tube 2.

For the resilient metal tube for the main tube 2, a tube made of a super-elastic metal or stainless steel (particularly stainless steel for spring) is suitable. When using such a resilient metal tube for the main tube 2, it is preferable that the metal tube is comparatively rigid over its proximal portion and comparatively flexible over its distal portion. By thus forming the metal tube, the manipulatability of the dilator can be further increased.

For the super-elastic metal or alloy for forming the metal tube, Ti—Ni alloy (Ni: 49 to 58 atomic percent), Cu—Zn alloy (Zn: 38.5 to 41.5 wt %), Cu—Zn—X alloy (X: 1 to 10 wt %, X: Be, Si, Sn, Al or Ga), and Ni—Al alloy (Al: 36 to 38 atomic percent) are preferable. The above Ti—Ni alloy is most preferable.

The main tube 2 formed of such a super-elastic metal has a length in the range of 300 to 4000 mm, preferably 500 to 3000 mm; an outer diameter in the range of 0.2 to 1.5 mm, preferably 0.3 to 1.2 mm; and a wall thickness in the range of 50 to 200 $\mu$m, preferably 80 to 150 $\mu$m. It also has a buckling strength (yield stress when increasing a load) in the range of 5 to 200 kg/mm2 (22° C.), preferably 8 to 150 kg/mm2 (22° C.) and a restoring stress (yield stress when decreasing a load) in the range of 3 to 180 kg/mm2 (22° C.), preferably 5 to 130 kg/mm2 (22° C.).

When using such a resilient metal tube, it is also preferable to coat the surface of the metal tube with a synthetic resin. Synthetic resins, such as thermoplastic resins [polyolefin (polyethylene, polypropylene, ethylene-propylene copolymer, etc.), polyvinyl chloride, ethylene-vinyl acetate copolymer, polyamide elastomer and polyurethane], fluororesin, and silicone rubber, can be used. Polyolefin, polyamide elastomer and polyurethane are preferable. It is preferable that the synthetic resin is sufficiently flexible not to hinder the metal tube from bending. The thickness of the plastic layer is in the range of 5 to 300 $\mu$m, preferably 10 to 200 $\mu$m.

The main tube 2 may also be made by using a metal tube as described above for the proximal portion longer than half the total length and connecting to the metal tube and a flexible plastic tube described above in order to make the distal portion flexible.

Figure 3:
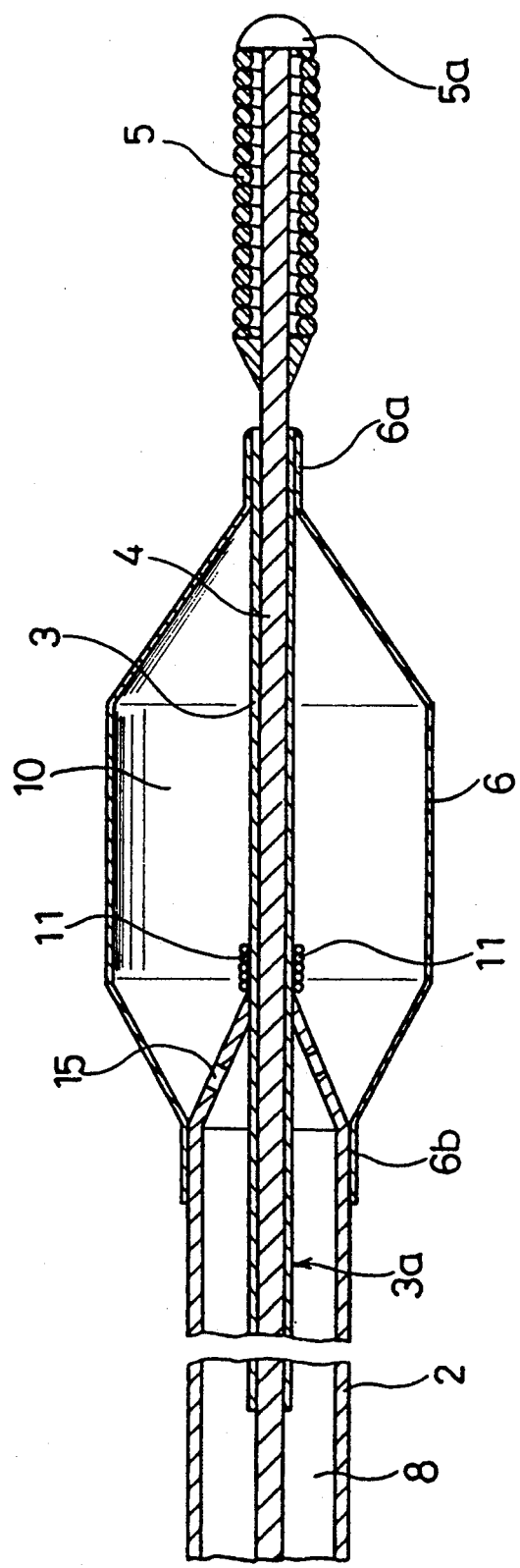
FIG. 3 is an enlarged cross-sectional view of the distal portion of the blood vessel dilator shown in FIG. 1.

The distal-end tube 3 is a tube open at both front and rear ends, whose a rear portion is situated in the distal end portion of the main tube 2 and the front end portion protrudes out of the distal end of the main tube 2, as shown in FIGS. 1 and 3. In the embodiment shown in FIGS. 1 and 3, the distal-end tube 3 has a substantially uniform diameter over its entire length. However, the distal-end tube 3 may also be formed so that the inside diameter of its front end portion is larger than that of the contact portion 3a. Further, the portion of the resilient core member 4 corresponding to the front end portion of the distal-end tube 3 may be formed thinner to make a space between the resilient core member 4 and the inside surface of the distal-end tube 3.

Figure 2:
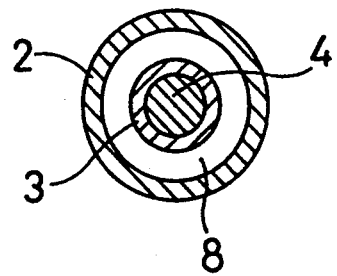
FIG. 2 is a cross-sectional view taken along the line I—I in FIG. 1.

In the embodiment shown in FIG. 1, the distal-end portion 3 is so formed that the inside diameter of the supporting portion 3a is substantially equal to or slightly larger than the diameter of the corresponding portion of the resilient core member 4, as shown in FIG. 2 showing the I—I section of FIG. 1. The lumen 8 thereby does not substantially communicate with the outside (and the space if formed) and leakage of the dilatation liquid substantially does not occur.

The resilient core member 4 can be turned around its axis, because the distal-end tube 3 and the resilient core member 4 are in contact with each other but not rigidly connected.

The distal-end tube 3 has a length in the range of 40 to 1000 mm, preferably 50 to 800 mm; an outside diameter in the range of 0.1 to 1.0 mm, preferably 0.15 to 0.8 mm; and a wall thickness of 10 to 150 $\mu$m, preferably 20 to 100 $\mu$m.

For the material for forming the distal-end tube 3, synthetic resins, such as polyimide and polyolefin (polyethylene, polypropylene, ethylene-propylene copolymer, ethylene-vinyl acetate copolymer, for example), can be used. Polyimide is preferable.

The distal-end tube 3 is connected to the distal end portion of the main tube 2 in such a manner that the communication between the lumen 8 in the main tube 2 and the inside of the dilatation element 6 is not blocked. Specifically, in the embodiment shown in FIG. 1, the distal end portion of the main tube 2 is tapered to diminish the diameter and connected with the distal-end tube 3. In the tapered wall of the main tube 2, bores or openings 15 are provided, through which the lumen 8 and the inside of the dilatation element 6 communicate with each other.

The distal-end tube 3 may also be connected to the main tube 2 by another method; inserting between them a ring insert with cuts on its periphery (forming passes connecting the lumen 8 and the inside of the dilatation element) and welding the insert, for example.

A marker 11 is provided on the external surface of the distal-end tube 3 at the position corresponding to the rear end of the cylindrical portion of the dilatation element 6 as shown in FIG. 3. The marker 11 is preferably formed in a spiral spring or ring. For the material for forming the marker 11, metals highly impervious to X rays, such as Pt, Pt alloy, W, W alloy, Ag, and Ag alloy, are preferable.

A leading guide 5 is provided on the distal end portion of the resilient core member 4 protruding out of the front end of the main tube 2. In this embodiment, the leading guide 5 is formed of a spiral spring, which is retained on the resilient core member 4 with both ends secured. The resilient core member 4 may be so formed that it becomes thinner gradually toward its distal end or its portion inside the leading guide 5 becomes thinner by step, in order to increase the flexibility of its distal end portion.

For the material of the resilient core member 4, stainless steel (preferably high-tensile-strength spring steel), tungsten, tungsten-cobalt alloy, piano wire (preferably nickel- or chrome-plated piano wire) and super-elastic metal or alloy, for example, can be used. For the super-elastic metal or alloy, Ti—Ni alloy (Ni: 49 to 58 atomic percent), Cu—Zn alloy (Zn: 38.5 to 41.5 wt %), Cu—Zn-X alloy (X: 1 to 10 wt %, X: Be, Si, Sn, Al or Ga), and Ni—Al alloy (Al: 36 to 38 atomic percent) are preferable. The above Ti—Ni alloy is most preferable. The resilient core member 4 has a length in the range of 450 to 2200 mm, preferably 550 to 1800 mm; a buckling strength (yield stress when increasing a load) in the range of 30 to 100 kg/mm2 (22° C.), preferably 40 to 55 kg/mm2 (22° C.); and a restoring force (yield stress when decreasing a load) in the range of 20 to 80 kg/mm2 (22° C.), preferably 30 to 35 kg/mm2 (22° C.). The diameter of the distal end portion of the resilient core member 4 is in the range of 0.1 to 1.0 mm, preferably 0.15 to 0.7 mm. The bending load is in the range of 0.1 to 10 g, preferably 0.3 to 6.0 g and a restoring load in the range of 0.1 to 10 g, preferably 0.3 to 6.0 g.

The distal end portion of the resilient core member 4 need not necessarily have a diameter within the above range over its entire length. It may partly have a diameter within the range. Further, the distal end portion and the other major portion of the resilient core member 4 need not have the same restoring stress, but preferably may have different properties; that is, the distal end portion a comparatively high flexibility and the major portion a comparatively large restoring stress. Such properties can be given by separate heat treatments or different diameters, for example. The resilient core member 4 may also be a stranded or unstranded wire formed of two or more wires, which can be given different properties along its length by the number of the wires in addition to heat treatments and diameters described above.

The leading guide 5 serves as the guide which leads the dilatation element 6 of the dilator 1 to the aimed region of a blood vessel. In the embodiment shown in FIG. 1, it is formed using a spiral spring. The leading guide 5 has a sufficient flexibility to readily bend when the tip comes into contact with the wall of a vessel and thereby prevent the concentration of force at the tip and allow the tip to change the course of advance along the vessel wall. Since the course of advance in blood vessels is selected using the leading guide 5, it is preferable that the position of the leading guide 5 can be easily observed by fluoroscopy. Therefore, for the material the leading guide 5, metals impervious to X rays, such as Pt, Pt alloy (Pt-Ir alloy, for example), W, W alloy, Ag, and Ag alloy, are preferable.

The leading guide 5 is also desired to be sufficiently flexible and may be formed using a spiral spring of an super-elastic or high-resilience metal wire. The leading guide 5 has preferably an outside diameter in the range of about 0.2 to 1.0 mm and a length in the range of about 2 to 50 mm. When an super-elastic or high elasticity metal wire is used, the buckling strength (yield stress when increasing a load) is within the range of 5 to 200 kg/mm2 (22° C.), preferably 8 to 150 kg/mm2 (22° C.) and the restoring force (yield stress when decreasing a load) is within the range of 3 to 180 kg/mm2 (22° C.), preferably 5 to 150 kg/mm2 (22° C.).

The front end 5a of the leading guide 5 is rounded to have a smooth concave surface by welding a very thin metal wire. The spiral spring forming the leading guide 5 and the resilient core member 4 are connected by brazing. It is preferable that the resilient core member 4 is extended up to the same position as the front end of the spring and the front end of the spring is connected to the extended distal end of the resilient core member 4, in order to prevent a permanent deformation of the spiral spring.

The front end portion of the dilatation element 6 is connected to the front end of the distal-end tube 3 and the rear end portion of the dilatation element 6 to the distal end of the main tube 2. The inside of the dilatation element 6 is in communication with the lumen 8 in the main tube 2 through the bores 15 provided in the distal end portion of the main tube 2, which allows the injection of a dilatation liquid into the dilatation element 6. The dilatation element 6 is inflatable and foldable or contractible when deflated. It has at least one substantially cylindrical portion of an approximately uniform diameter for expanding a stenotic lesion in a blood vessel. This portion may also be a prism instead of a cylinder.

The cylindrical portion of the dilatation element 6 has an outside diameter in the range of 1.0 to 10 mm, preferably 1.0 to 5.0 mm and a length in the range of 5 to 50 mm, preferably 10 to 40 mm when the dilatation element 6 is inflated. The overall length of the dilatation element 6 is in the range of 10 to 70 mm, preferably 15 to 60 mm.

For the dilatation element 6, materials which can be used in blood vessels without causing problems and have a certain amount of flexibility are preferable. Thermoplastic resins [polyolefin (polyethylene, polypropylene, ethylene-propylene copolymer, etc.), polyester (polystylene terephthalate, etc.), polyvinyl chloride, ethylene-vinyl acetate copolymer, ethylene-vinyl acetate crosslinked copolymer, polyurethane, polyphenylenesalfide], polyamide elastomer, silicone rubber, and latex rubber, for example, can be used.

Figure 4:
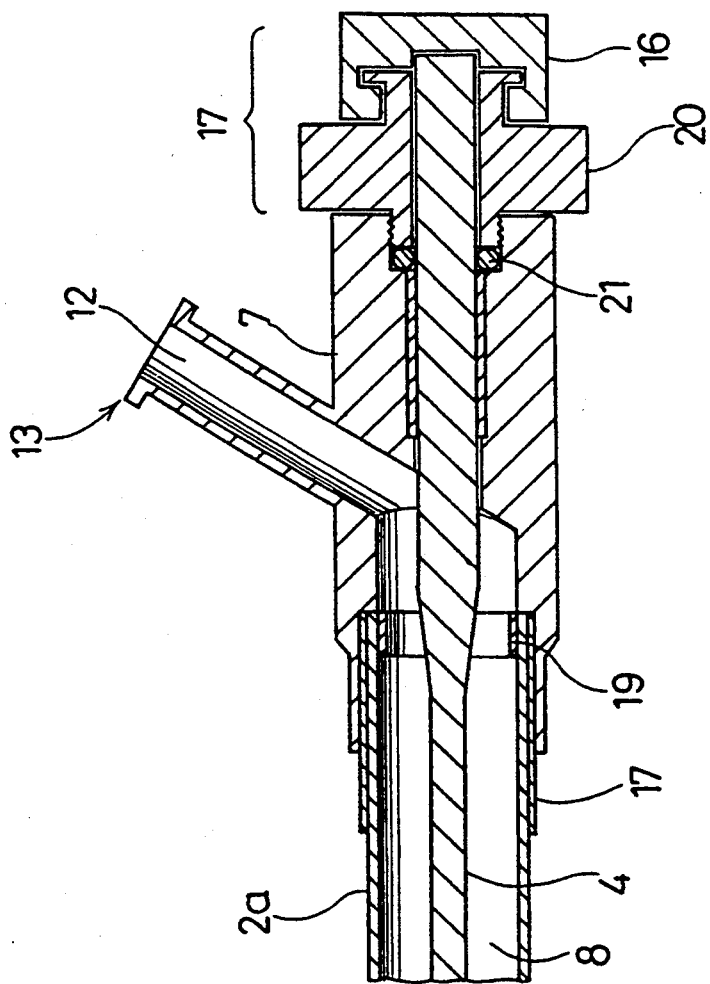
FIG. 4 is an enlarged cross-sectional view of the proximal portion of the blood vessel dilator shown in FIG. 1.
Figure 5:
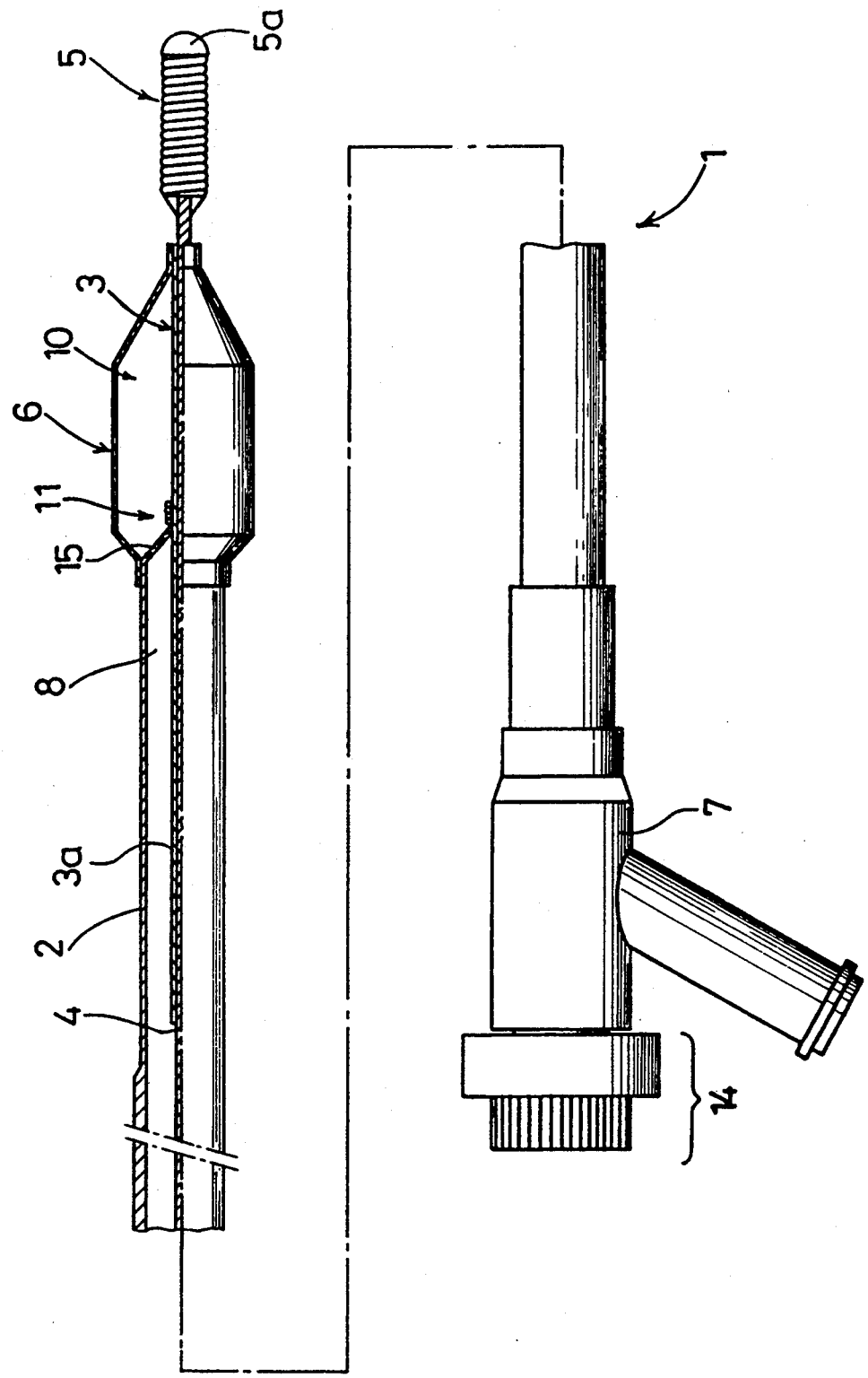
FIG. 5 is a cross-sectional view of a part of the second embodiment of the blood vessel dilator according to the present invention.

The main-tube hub 7 is connected to the proximal end of the main tube 2 as shown in FIGS. 1 and 4. It has an opening or bore 12 which communicates with the lumen 8. The opening 12 serves as the dilatation liquid injection port. For the material for the main-tube hub 7, thermoplastic resins such as polycarbonate, polyamide, polysulfone, polyallylate and methacrylate-butylene-styrene-copolymer can be used.

Specifically in this embodiment, as shown in FIG. 4, the main-tube hub 7 is connected to the distal end portion 2a of the main tube 7 and provided with a first bore for putting through the resilient core member 4 and a second bore or opening 12 which is in communication with the lumen 8 and serves as the injection port of a dilatation liquid. The proximal end portion of the main tube 2 is reinforced by a reinforcing tube 17 for preventing the main tube 2 from kinking. The main-tube hub 7 and the reinforcing tube 17 may be bonded by applying an adhesive between their contacting surfaces.

The core-member hub 14 comprises a locking screw 20 for locking or releasing the resilient core member 4 and a turning knob 16 rotatably attached to the locking knob 20. An O-ring 21 is put in the bore between the front end of the locking screw 20 and the radial surface formed in the bore. The resilient core member 4 can be locked or released by the locking screw 20 and the O-ring 21. When the locking screw 20 is tightened, the O-ring deforms and presses against the resilient core member 4. The resilient core member 4 is thereby held firmly so as not to turn in the main tube 2, and the gap between the main-tube hub 7 and the resilient core member 4 is sealed liquid-tight. When the locking screw 20 is not tightened, the resilient core member 4 is free to turn. The turn knob 16 is connected to the proximal end of the resilient core member 4. By turning the turn knob 16, the leading guide 5 at the distal end of the resilient core member 4 can be turned through the resilient core member 4. The turn knob 16 is attached to the locking screw 20 so that it can turn around the axis but cannot move lengthwise. For the material of the core-member hub 14, specifically the locking screw 20 and the turn knob 16, thermoplastic resins such as polycarbonate, polyamide, polysulfone, polyallylate and methacrylate-butylene-styrene-copolymer can be used.

It is preferable to coat the outside surfaces of the main tube 2, the dilatation element 6 and the leading guide 5 with an appropriate lubrication-imparting agent. For the lubricant, hydrophilic polymers such as poly(2-hydroxyethylmethacrylate), polyhydroxyethylacrylate, hydroxypropylcellulose, methyl vinyl ether-maleic anhydride copolymer, polyethylen glycol, polyacrylamide, polyvinylpyrrolidone are preferable. Further, it is also preferable to coat the inside surface of the distal-end tube 3 which supports the resilient core member 4 or the surface of the resilient core member 4 which is in contact with the distal-end tube 3 or both of them with teflon or an appropriate lubrication-imparting agent as listed above.

Figure 6:
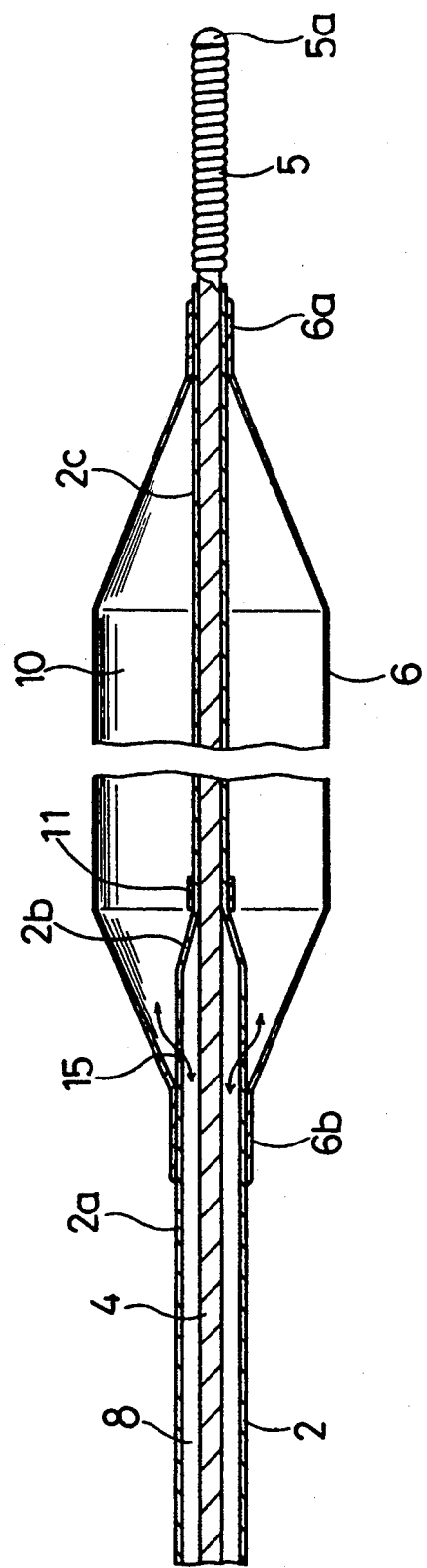
FIG. 6 is an enlarged cross-sectional view of the distal portion of the blood vessel dilator of another embodiment.

Another embodiment shown in FIG. 6 is described below.

FIG. 6 is an enlarged sectional view of the distal end portion of another embodiment of the blood vessel dilator according to the present invention.

The blood vessel dilator of this embodiment comprises a main tube 2 which has a thinner portion 2c formed at the distal end side and a thicker major portion 2a; a dilatation element 6 having a front end portion 6a connected to the front end portion of the thinner portion 2c of the main tube 2 and a rear end portion connected to the distal end portion of the major portion 2a of the main tube 2; a resilient core member 4 put through the inside of the main tube 2; a leading guide 5 provided at the distal end portion of the resilient core member 4; a lumen 8 formed between the major portion 2a of the main tube 2 and the resilient core member 8; a hole or bore 15 for communicating the lumen 8 and the inside of the dilatation element 6 with each other, provided in the distal end portion of the major portion 2a of the main tube 2; a main-tube hub 2 connected to the proximal end of the main tube 2 and provided with a bore 12 communicating with the lumen 8; and a core-member hub 14 connected to the proximal end of the resilient core member 4 and serving as a means of turning the resilient core member 4 with respect to the main tube 2. The thinner portion 2c of the main tube 2 has a supporting portion 3a so formed that the inside diameter is substantially equal to or slightly larger than the diameter of the resilient core member 4.

The main tube 2 is a tube with a certain amount of flexibility, formed of a flexible plastic or a resilient metal. It may also be formed by connecting a distal portion formed by a flexible plastic and a proximal portion formed of a super-elastic metal. For the plastic material for the main tube 2, synthetic resins with a good flexibility, such as thermoplastic resins [polyolefin (polyethylene, polypropylene, ethylene-propylene copolymer, ethylene-vinylacetate copolymer, a blend of polypropylene and polybutene), polyvinyl chloride, polyamide elastomer and polyurethane] and polyimide, can be used. Polyolefin and polyimide are preferable. The main tube 2 formed of such a plastic material has an overall length in the range of 300 to 2000 mm, preferably 500 to 1600mm; a length of the thinner portion 2c in the range of 10 to 100 mm, preferably 20 to 50 mm; a length of the major portion 2a in the range 300 to 2000 mm, preferably 500 to 1500 mm; an outside diameter of the thinner portion 2c in the range of 0.05 to 0.3 mm, preferably 0.1 to 0.2 mm; an outside diameter of the major portion in the range of 0.3 to 1.5 mm, preferably 0.4 to 1.2 mm, and a wall thickness in the range of 30 to 200 μm, preferably 50 to 150 μm.

For the resilient metal tube for the main tube 3, a tube made of a super-elastic metal or stainless steel (particularly stainless steel for spring) is preferable. When such a resilient metal tube is used for the main tube 2, it is preferable to form the tube so that the proximal portion is comparatively rigid and the distal portion flexible. By thus forming the metal tube, the manipulatability of the dilator can be further increased.

For the super-elastic metal for the main tube 2, Ti—Ni alloy (Ni: 49 to 58 atomic percent), Cu—Zn alloy (Zn: 38.5 to 41.5 wt %), Cu—Zn-X alloy (X: 1 to 10 wt %, X: Be, Si, Sn, Al or Ga), and Ni—Al alloy (Al: 36 to 38 atomic percent) are preferable. Ti—Ni alloy is most preferable.

The main tube 2 formed of such a super-elastic metal has an overall length in the range of 300 to 4000 mm, preferably 500 to 3000 mm; an outside diameter in the range of 0.2 to 1.5 mm, preferably 0.3 to 1.2 mm, and a wall thickness in the range of 50 to 200 μm, preferably 80 to 150 μm, a buckling strength (yield stress when increasing a load) in the range of 5 to 200 kg/mm2 (22° C.), preferably 8 to 150 kg/mm2 (22° C.); and a restoring stress (yield stress when decreasing a load) in the range of 3 to 180 kg/mm2 (22° C.), preferably 5 to 130 kg/mm2 (22° C.).

When using a metal tube for the main tube 2, it is preferable to coat the outside surface of the tube with a synthetic resin. Synthetic resins, such as thermoplastic resins [polyolefin (polyethylene, polypropylene, ethylene-propylene copolymer, etc.), polyvinyl chloride, ethylenevinyl acetate copolymer, polyamide elastomer and polyurethane], fluororesin, and silicone rubber, can be used. Polyolefin, polyamide elastomer and polyurethane are preferable. The synthetic resin is desired to be sufficiently flexible not to hinder the metal tube from bending. The thickness of the synthetic resin is in the range of 5 to 300 μm, preferably 10 to 200 μm.

The main tube 2 may also be made by using a metal tube as described above for the proximal portion longer than half the total length of a main tube 2 and connecting to it a tube formed of a synthetic resin as listed above, in order to make the distal portion more flexible.

In this embodiment, the thinner portion 2c of the main tube 2 is so formed that the inner diameter is substantially equal to or slightly larger than the diameter of the corresponding portion of the resilient core member 4. The lumen 8 thereby does not substantially communicate with the outside and leakage of the dilatation liquid substantially does not occur. Since the resilient core member 4 is rotatably supported and not firmly secured by the thinner portion 2c of the main tube 2, it can turn around its axis in the main tube.

The main-tube hub and the core-member hub connected to the main tube 2 and the resilient core member 4 (not shown) may be the same as those shown in FIG. 4 and described above. The dilatation element 6 and the leading guide 5 may also be the same as those shown in FIGS. 3 and 4 and described above.

Figure 7:
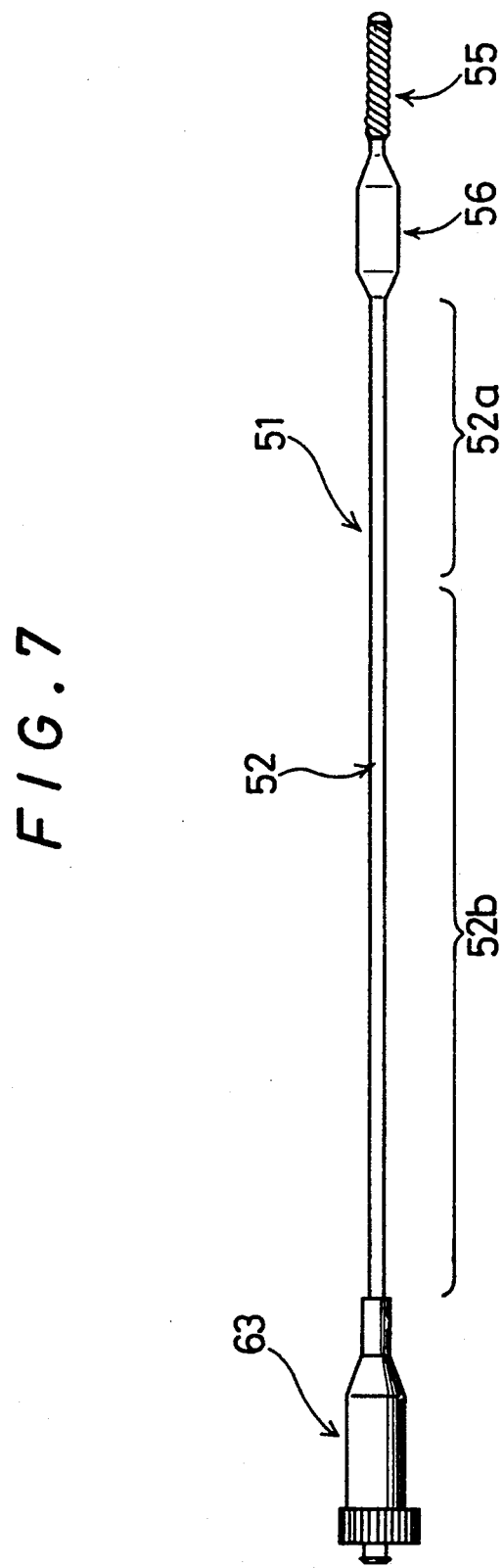
FIG. 7 is a general view of the blood vessel dilator of the third embodiment.
Figure 8:
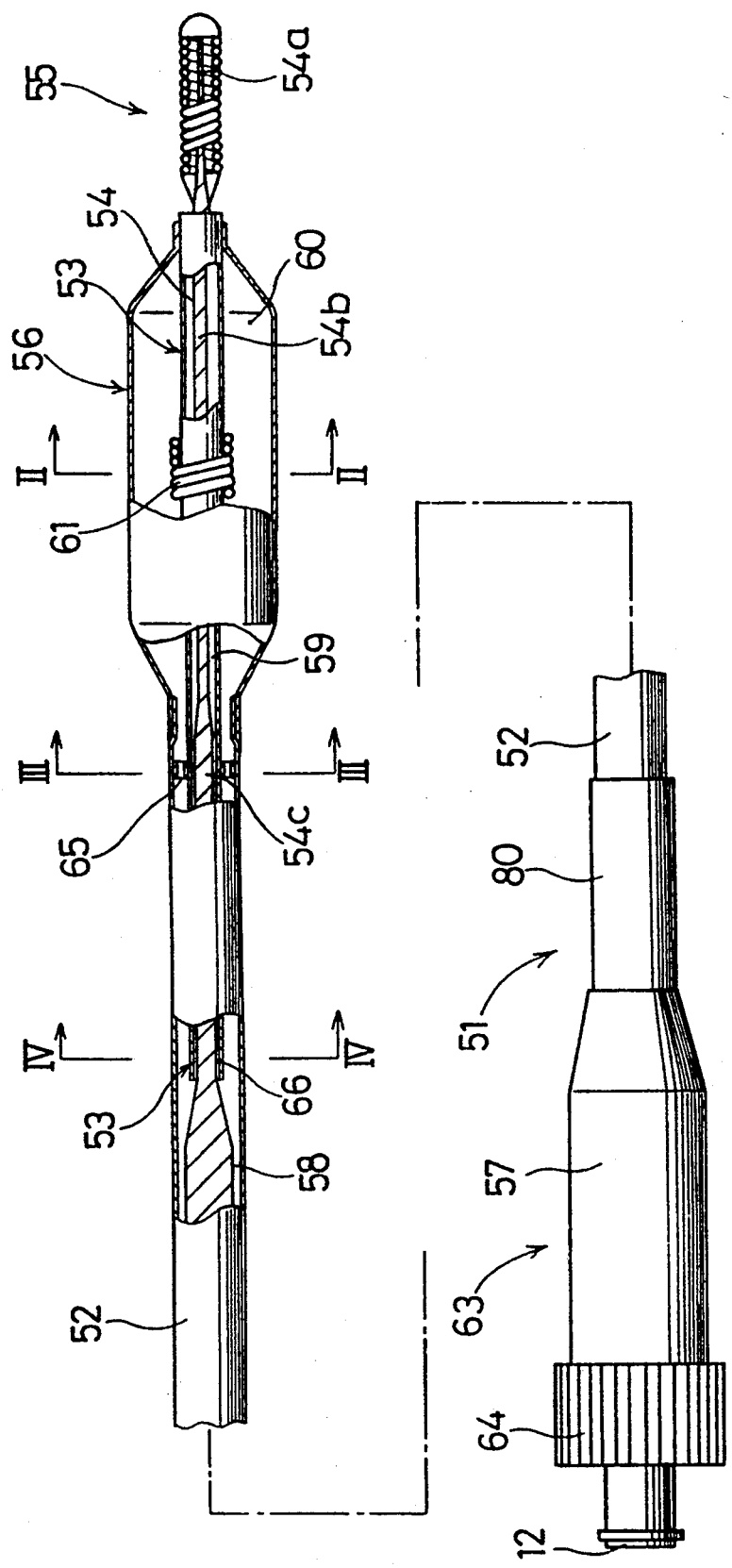
FIG. 8 is a diagrammatic partial cross-sectional view of the distal portion of the blood vessel dilator shown in FIG. 7.

The third embodiment of the present invention shown in FIGS. 7 and 8 is described below.

The blood vessel dilator 51 of this embodiment comprises a main tube 52 having a lumen 58; a distal-end tube 53 put in the distal end portion of the main tub 52 and protruding out of the distal end of the main tube 52; a contractible or foldable dilatation element 56 with its front end portion connected to the distal-end portion and its rear end portion to the distal end portion of the main tube 52; a resilient core member 54 put through the inside of the main tube 52 and the distal-end tube 53; a leading guide 55 provided at the distal end of the resilient core member 54; a main-tube hub 57 connected to the proximal end of the main tube 52 and provided with a opening 12 or 62 communicating with the lumen 58; and a core-member hub 54 connected to the proximal end of the resilient core member 64 and serving as a means of turning the resilient core member 54 with respect to the main tube 52. The distal-end tube 53 has a supporting portion 53a whose an inside diameter is substantially equal to or slightly larger than the corresponding portion of the resilient core member 54.

The blood vessel dilator 51 of this embodiment is described below using FIGS. 7 to 14 below.

Figure 9:
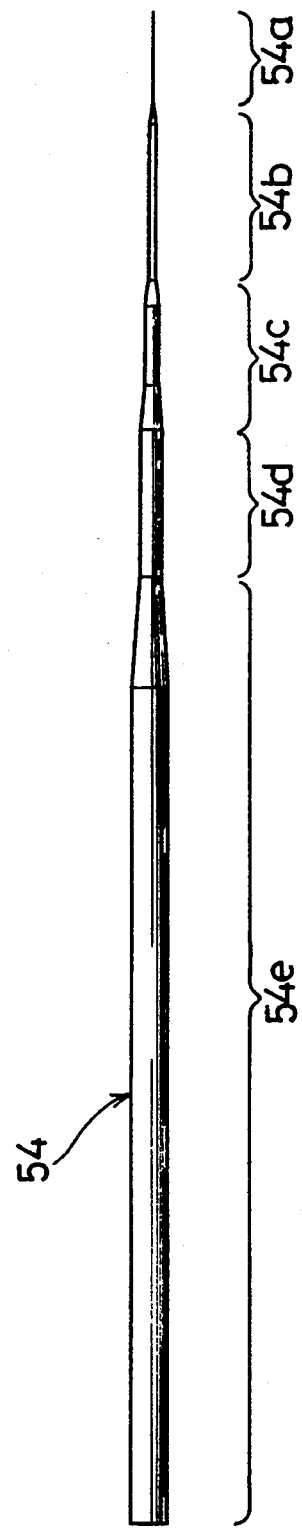
FIG. 9 is an external view of an example of the resilient core member used for the blood vessel dilator of the present invention.
Figure 10:
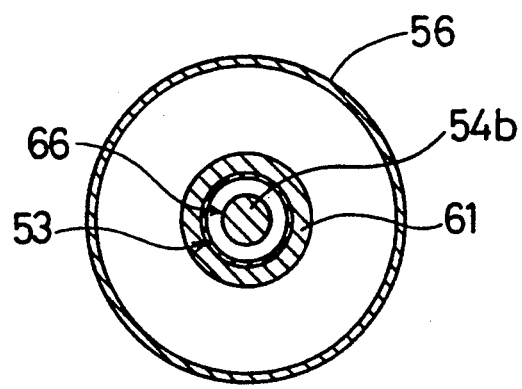
FIG. 10 is a cross-sectional view along the line II—II in FIG. 8.
Figure 13:
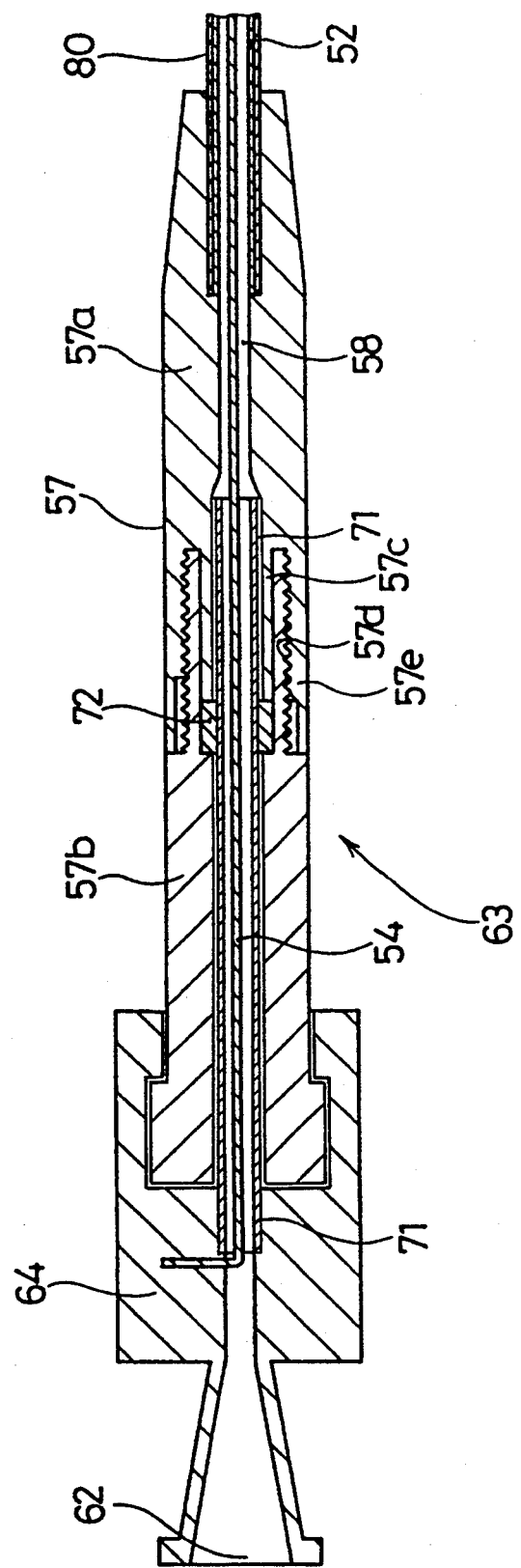
FIG. 13 is a cross-sectional view of an example of the hub assembly used for the blood vessel dilator of the present invention.
Figure 14:
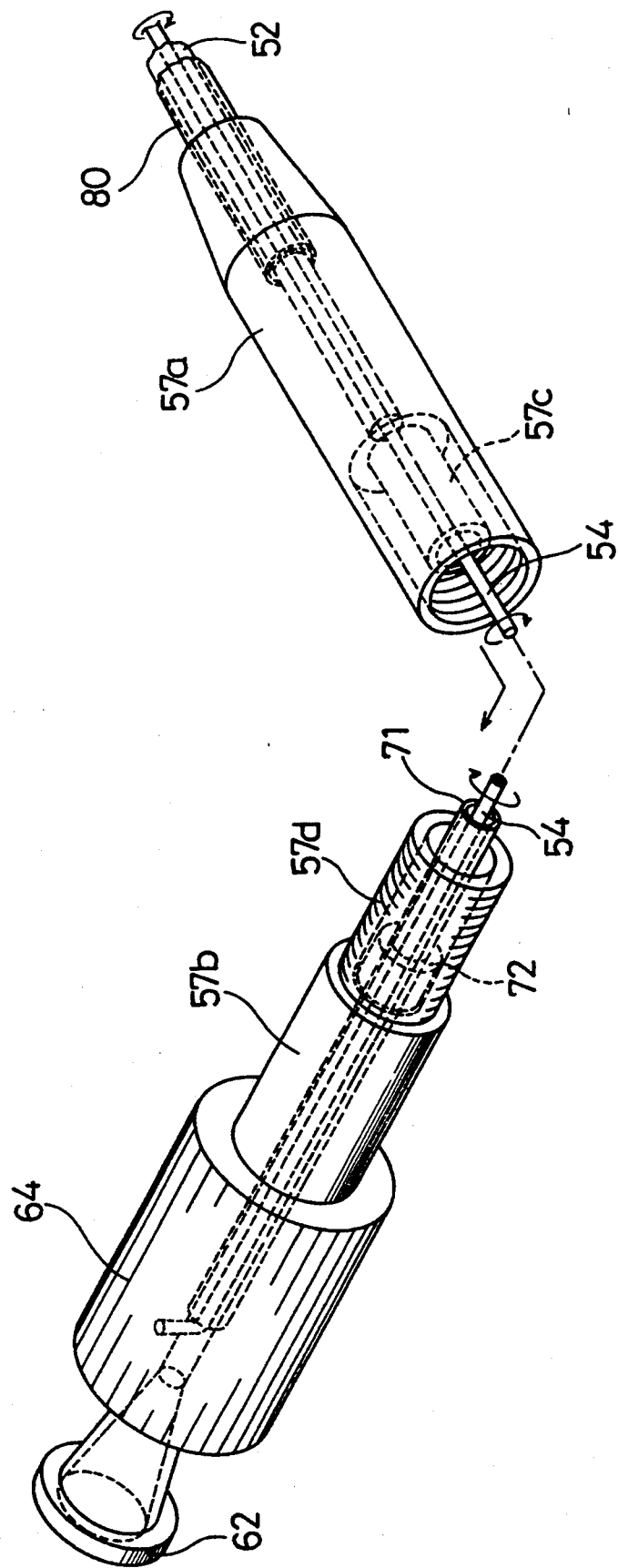
FIG. 14 is a diagrammatic view of the hub assembly shown in FIG. 13.

FIG. 7 is a general view of the blood vessel dilator 51, FIG. 8 is an enlarged sectional view of the distal end portion of the blood vessel dilation 51, FIG. 9 is an external view of an example of the resilient core member 54, FIG. 13 is a sectional view of an example of the hub assembly 63, and FIG. 14 is a diagrammatic view of the hub assembly of FIG. 13.

The blood vessel dilator 51 of this embodiment comprises a main tube 52, a distal-end tube 53, a resilient core member 54, a dilatation element 56, and a hub assembly 63.

The main tube 52 supports the distal-end tube 53 coaxially in it. Its distal end is situated a little behind the front end of the distal-end tube 53, and its proximal end is extended long behind the rear end of the distal-end tube 53.

The main tube 2 is a tube with a certain amount of flexibility, formed of a flexible plastic or a resilient metal. It may also be formed by connecting a distal portion formed by a flexible plastic and a proximal portion formed of a resilient metal (super-elastic metal tube, for example). For the plastic material for the main tube 2, synthetic resins with a good flexibility, such as thermoplastic resins [polyolefin (for example, polyethylene, polypropylene, ethylene-propylene copolymer, ethylene-vinylacetate copolymer, a blend of polypropylene and polybutene,), polyvinyl chloride, polyamide elastomer and polyurethane] and polyimide, can be used. Polyolefin and polyimide are preferable. The main tube 2 formed of such a plastic material has a length in the range of 300 to 2000mm, preferably 500 to 1600 mm; an outside diameter in the range of 0.3 to 1.5 mm, preferably 0.4 to 1.2 mm, and a wall thickness in the range of 30 to 200 µm, preferably 50 to 150 µm. It is also preferable that the main tube 53 has a length two times or more greater than that of the distal-end tube 53, in other words the distal-end tube 53 is less than half the length of the main tube 52.

For the resilient metal tube for the main tube 53, a tube made of a super-elastic metal or stainless steel (particularly stainless steel for spring) is preferable. When such a resilient metal tube is used for the main tube 2, it is preferable to form the metal tube so that its proximal portion is comparatively rigid and its distal portion flexible. By thus forming the main tube 52, the manipulatability of the dilator can be further increased.

For the super-elastic metal for the main tube 2, Ti—Ni alloy (Ni: 49 to 58 atomic percent), Cu—Zn alloy (Zn: 38.5 to 41.5 wt %), Cu—Zn-X alloy (X: 1 to 10 wt %, X: Be, Si, Sn, Al or Ga), and Ni—Al alloy (Al: 36 to 38 atomic percent) are preferable. The above Ti—Ni alloy is most preferable.

The main tube 2 formed of such a super-elastic metal has a length in the range of 300 to 4000 mm, preferably 500 to 3000 mm; an outer diameter in the range of 0.2 to 1.5 mm, preferably 0.3 to 1.2 mm; and a wall thickness in the range of 50 to 200 µm, preferably 80 to 150 µm. It also has a buckling strength (yield stress when increasing a load) in the range of 5 to 200 kg/mm2 (22° C.), preferably 8 to 150 kg/mm2 (22° C.) and a restoring stress (yield stress when decreasing a load) in the range of 3 to 180 kg/mm2 (22° C.), preferably 5 to 130 kg/mm2 (22° C.).

When using a metal tube for the main tube 2, it is preferable to coat the outside surface of the tube with a synthetic resin. Synthetic resins, such as thermoplastic resins [polyolefin (polyethylene, polypropylene, ethylene-propylene copolymer, etc.), polyvinyl chloride, ethylene-vinylacetate copolymer, polyamide elastomer and polyurethane], fluororesin, and silicone rubber, can be used. Polyolefin, polyamide elastomer and polyurethane are preferable. It is preferable that the synthetic resin is sufficiently flexible not to hinder the metal tube from bending. The thickness of the plastic layer is in the range of 5 to 300 µm, preferably 10 to 200 µm.

The main tube 2 may also be made by using a metal tube as described above for the proximal portion longer than half the total length and connecting to the metal tube a plastic tube described above in order to make the distal portion flexible.

The distal-end tube 53 is a tube open at both front and rear ends, whose rear end portion is put in the distal end portion of the main tube 52 and front end portion protrudes out of the distal end of the main tube 52 as shown in FIG. 8. In the embodiment shown in FIG. 8, the distal-end tube 53, over the entire length, has an inside diameter substantially equal to or slightly larger than the diameter of the corresponding portion of the resilient core member 54 and forms a contact portion 66 which supports the resilient core member 54 movably and liquid-tight.

Since the inside diameter of the distal-end tube 53 at the contact portion 66 is so formed as to be substantially equal to or slightly larger than the diameter of the corresponding portion of the resilient core member 54 as described above and shown in FIG. 12 of the sectional view along the IV—IV line in FIG. 8, the lumen 58 between the main tube 52 and the resilient core member 54 is substantially not in communication with the outside and therefore leakage of the dilatation liquid substantially does not occur.

Further, the resilient core member 54 thus being rotatably supported and not firmly secured by the contact portion 66, it can turn around its axis in the main tube 52.

The distal-end tube 53 has a length in the range of 40 to 1000 mm, preferably 50 to 800 mm; an outside diameter in the range of 0.1 to 1.0 mm, preferably 0.15 to 0.8 mm; and a wall thickness of 10 to 150 µm, preferably 20 to 100 µm.

For the material of the distal-end tube 53, polyimide and polyolefin (polyethylene, polypropylene, ethylene-propylene copolymer, ethylene-vinyl acetate copolymer, etc.), for example, can be used, and polyimide is preferable.

Figure 11:
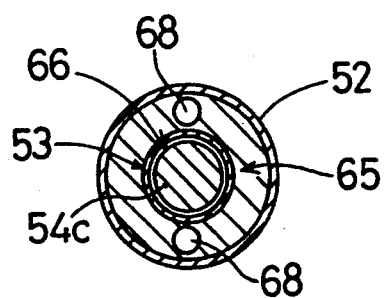
FIG. 11 is a cross-sectional view along the line III—III in FIG. 8.
Figure 12:
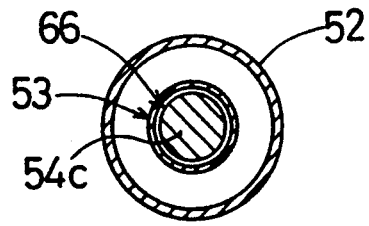
FIG. 12 is a cross-sectional view along the line IV—IV in FIG. 8.

The main tube 52 and the distal-end tube 53 are connected without blocking the combination between the lumen 58 and the inside of the dilatation element 56. Specifically in this embodiment, a ring insert (fixing member) 65 is put between the main tube 52 and the distal-end tube 53 at a position a little to the proximal side from the distal end of the main tube 52, and the main tube 52 and the distal-end tube 53 are connected by means of the insert 65 as shown in FIG. 8. As shown in FIG. 11, the sectional view along the II—II line in FIG. 8, the insert 65 is provided with holes 68, through which the lumen 58 in the main tube 52 and the inside of the dilatation element 56 communicates with each other. For the material of the insert 65, those which can be welded by heating are preferable, for example, hot melt resin or hot melt adhesive. For hot melt resin or hot melt adhesive, ethylene-vinylacetate copolymer, ethylene-acrylic ester copolymer, polyamide resin can be used. An appropriate adhesive bond may be used instead of welding. For the adhesive, epoxy resin adhesive, polyurethane adhesive, polyvinylether adhesive, vinylacetate copolymer can be used. The above epoxy resin adhesive is preferable.

It is preferable that a marker 61 is provided on the outside surface of the distal-end tube 53 at the position corresponding to the middle of the cylindrical portion. The marker 61 is preferably formed in a spiral spring or ring. For the material of the marker 61, metals highly impervious to X rays, such as Pt, Pt alloy, W, W alloy, Ag, and Ag alloy are preferable.

The resilient core member 54 comprises a portion housed in the main tube 52 and distal-end tube 53 and a leading guide portion protruding out of the front end of the distal-end tube 53. In this embodiment, a spiral spring is attached to the leading guide portion to form a leading guide 55. The leading guide portion of the resilient core member 54 extends through the spiral spring up to the front end of the spring. The spring is secured to the resilient core member 54 at both ends.

It is preferable that the distal portion of the resilient core member 54 is flexible. For this reason, the resilient core member 54 of this embodiment is so formed that it has a plurality of portions whose diameters stepwise becoming smaller and connected by tapered portions between them, that is, a major proximal portion 54e, the first to third middle portions 54d to 54b and a distal-end portion 54a as shown in FIG. 9. The first middle portion 54d has an diameter smaller than a diameter of the major proximal portion 54e. The second middle portion 54c has an diameter smaller than a diameter of the first middle portion 54d. The third middle portion 54b has an diameter smaller than a diameter of the second middle portion 54c. The distal-end portion 54a has an diameter smaller than a diameter of the third middle portion 54b. As shown in FIG. 8, the diameter of the second middle portion 54c is substantially equal to or slightly smaller than the inside diameter of the rear end portion of the distal-end tube 53. The second middle portion 54c is thus supported movably and substantially liquid-tight by the corresponding portion (contact portion 66) of the distal-end tube 53. The proximal side end of the third middle portion 54b is situated around the distal end of the main tube 52 (the rear end of the distal-end tube 53) and the distal side end around the front end of the distal-end portion 53 (the front end of the dilatation element 56) as shown in FIG. 8. The diameter of this third middle portion 54b is smaller than the inside diameter of the corresponding portion of the distal-end tube 53, and a space 59 is made between the resilient core member 54 and the inside surface for the distal-end tube 53 as shown in FIG. 8. The distal end portion 54a has preferably a flat cross section. By thus forming the cross section of the distal end portion 54a, the distal end portion 54a becomes ore flexible.

When forming the proximal portion or the whole of the main tube 52 of an aforementioned super-elastic metal, the main tube 52 has a sufficient pushability, allowing use of a resilient core member with a decreased pushability, specifically one whose major proximal portion 5e has about the same diameter as the first middle portion 5d, for example. As a result, the lumen 58 can have a greater cross section, and injection of the dilatation liquid is thereby made easier.

Further, it is preferable to apply a lubricant between the inside surface of the contact portion 66 of the distal-end tube 53 and the surface of the corresponding second middle portion 54c of the resilient core member 56. By thus applying a lubricant, the friction between the distal-end tube 53 and the resilient core member 56 can be reduced and the turn of the core member 56 thereby becomes smoother. The lubricant also serves to prevent the leakage of the dilatation liquid and hence to maintain the pressure of the liquid injected in the lumen 58. In addition, the entrance of the blood from the front end of the distal-end tube 53 into the lumen 58 can be prevented. In other words, the lubricant is a closing agent to close a space formed between the second middle portion 54c of the core member 54 and the contact portion 66 of the distal-end tube 53.

For the lubricant, silicone oil is preferable.

Instead of applying a lubricant, it may also be preferable to coat the inside surface of the contact portion 66 of the distal-end tube 53 or the surface of the corresponding second middle portion 54c of the resilient core member 56 or both of them with a resin for reducing friction such as fluororesin (PTFE, ETFE, etc.) to facilitate the turning manipulation of the resilient core member 54.

For the material of the resilient core member 54, stainless steel (preferably high-tensile-strength spring steel), tungsten, tungsten-cobalt alloy, piano wire (preferably nickel- or chrome-plated piano wire) and super-elastic metals, for example, can be used. Ti—Ni alloy (Ni: 49 to 58 atomic percent), Cu—Zn alloy (Zn: 38.5 to 41.5 wt %), Cu—Zn-X alloy (X: 1 to 10 wt %, X: Be, Si, Sn, Al or Ga), and Ni—Al alloy (Al: 36 to 38 atomic percent) are preferable. The above Ti—Ni alloy is most preferable. The resilient core member 4 has a length in the range of 450 to 2200 mm, preferably 550 to 1800 mm; a buckling strength (yield stress when increasing a load) in the range of 30 to 100 kg/mm2 (22° C.), preferably 40 to 55 kg/mm2 (22° C.); and a restoring force (yield stress when decreasing a load) in the range of 20 to 80 kg/mm2 (22° C.), preferably 30 to 35 kg/mm2 (22° C.). The diameter of the distal end portion of the resilient core member 4 is in the range of 0.1 to 1.0 mm, preferably 0.15 to 0.7 mm. The bending load is in the range of 0.1 to 10 g, preferably 0.3 to 6.0 g and a restoring load in the range of 0.1 to 10 g, preferably 0.3 to 6.0 g.

The distal end portion of the resilient core member 4 need not necessarily have a diameter within the above range over its entire length. It may partly have a diameter within the range. Further, the distal end portion and the other major portion of the resilient core member 4 need not have the same restoring stress, but preferably may have different properties; that is, the distal end portion a comparatively high flexibility and the major portion a comparatively large restoring stress. Such properties can be given by separate heat treatments or different diameters, for example. The resilient core member 4 may also be a stranded or unstranded wire formed of two or more wires, which can be given different properties along its length by the number of the wires in addition to heat treatments and diameters described above.

The leading guide 55 serves as the guide which leads the dilatation element 56 of the dilator 51 to the aimed region of a blood vessel. In the embodiment shown in FIG. 8, it is formed using a spiral spring. The leading guide 55 has a sufficient flexibility to readily bend when the tip comes into contact with the wall of a vessel and thereby prevent the concentration of force at the tip and allow the tip to change the course of advance along the vessel wall. Since the course of advance in blood vessels is selected using the leading guide 55, it is preferable that the position of the leading guide 55 can be easily observed by fluoroscopy. Therefore, for the material of the leading guide 55, metals impervious to X rays, such as Pt, Pt alloy (Pt-Ir alloy, for example), W, W alloy, Ag, and Ag alloy, are preferable.

The leading guide 55 is also desired to be sufficiently flexible and may be formed using a spiral spring of an super-elastic or high-resilience metal wire. The leading guide 55 has preferably an outside diameter in the range of about 0.2 to 1.0 mm and a length in the range of about 2 to 50 mm. When using a super-elastic metal wire, the buckling strength (yield stress when increasing a load) is in the range of 5 to 200 kg/mm2 (22° C.), preferably 8 to 150 kg/mm2 (22° C.) and the restoring force (yield stress when decreasing a load) in the range of 3 to 180 kg/mm2 (22° C.), preferably 5 to 150 kg/mm2 (22° C.).

The front end of the leading guide 55 is rounded to have a smooth concave surface by welding a very thin metal wire. The spiral spring forming the leading guide 55 and the resilient core member 54 are connected by brazing. It is preferable that the resilient core member 54 is extended up to the same position as the front end of the spring and the front end of the spring is connected to the extended distal end of the resilient core member 54, in order to prevent a permanent deformation of the spiral spring.

The front end portion of the dilatation element 56 is connected to the front end of the distal-end tube 53 and the rear end portion of the dilatation element 56 to the distal end of the main tube 52. The inside of the dilatation element 56 is in communication with the lumen 58 through the openings 68 provided in the insert 65, which allows the injection of a liquid into the dilatation element 56. The dilatation element 56 is inflatable and contractible or foldable when deflated. It has at least one substantially cylindrical portion of an approximately uniform diameter for expanding a stenotic lesion in a blood vessel. This portion may also be a prism instead of a cylinder.

The cylindrical portion of the dilatation element 56 has an outside diameter in the range of 1.0 to 10 mm, preferably 1.0 to 5.0 mm and a length in the range of 5 to 50 mm, preferably 10 to 40 mm when the dilatation element 56 is inflated. The overall length of the dilatation element 6 is in the range of 10 to 70 mm, preferably 15 to 60 mm.

For the dilatation element 56, materials which can be used in blood vessels without causing problems and have a certain amount of flexibility are preferable. Thermoplastic resins [polyolefin (polyethylene, polypropylene, ethylene-propylene copolymer, etc.), polyester (polystylene terephthalate, etc.), polyvinyl chloride, ethylene-vinyl acetate copolymer, ethylene-vinyl acetate crosslinked copolymer, polyurethane, polyphenylenesulfide], polyamide elastomer, silicone rubber, and latex rubber, for example, can be used. Thermoplastic resins [polyolefin (polyethylene, polypropylene, ethylene-propylene copolymer, etc.), polyester (polystylene terephthalate, etc.), polyvinyl chloride, ethylene-vinyl acetate copolymer, ethylene-vinyl acetate crosslinked copolymer, polyurethane], polyamide elastomer, silicone rubber, and latex rubber, for example, can be used.

As shown in FIG. 13, a sectional view of the proximal portion of the blood vessel dilator 51 shown in FIGS. 7 and 8, a hub assembly 63 comprises a main-tube hub 57 and a core-member hub 64. The main-tube hub 57 consists of two main-tube-hub members 57a and 57b. The first main-tube-hub member 57a is connected to the proximal end of the main tube 52. The proximal end of the main tube 52 is reinforced by a reinforcing tube 80 for preventing the kinking of the main tube 52. The first main-tube-hub member 57a and the reinforcing tube 80 may be bonded by applying an adhesive between their contacting surfaces. A comparatively deep annular recess is provided in the rear end portion of the first main-tube-hub member 57a to form an inner cylindrical projection 57c and an outer cylindrical portion 57e as shown in FIGS. 13 and 14. The end of the inner cylindrical projection 57c and an outer cylindrical portion 57e as shown in FIGS. 13 and 14. The inner cylindrical projection 57c is a little shorter than the outer cylindrical projection 57e as shown in FIG. 13. The first threaded portion is formed in the base area except the open-end area of the inside surface of the outer cylindrical projection 57e. In the front end of the second main-tube-hub member 57b, a cylindrical projection 57d protruding frontward is provided. The cylindrical projection 57d has an inside diameter substantially equal to or slightly larger than the outside diameter of the inner cylindrical projection 57c of the first main-tube-hub member 57a so that it can receive the inner cylindrical projection 57c. Formed in the outside surface of the cylindrical projection 57d is the second threaded portion which engages with the first threaded portion formed in the first main-tube-hub member 57a.

A sealing ring member 72 is put in the cylindrical projection 57d of the second main-tube-hub member 57b. The ring 72 can be pressed between the open-side end of the inner cylindrical projection 57c of the first main-tube-hub member 57a and the radial surface (stepped portion) formed at the bottom of the cylindrical projection 57d of the second main-tube-hub member 57b when the second main-tube-hub 72b is driven into the first main-tube-hub 72a.

For the material of the sealing ring member 72, elastic materials such as rubbers (silicone rubber, butadiene rubber, etc.) and elastomers [styrene-derived elastomers (SBS, SEBS, etc.), polyolefin elastomer, polyamide elastomer, etc.] can be used.

For the material of the main-tube hub members 57a and 57b, thermoplastic resins such as polycarbonate, polyamide, polysulfone, polyallylate and methacrylate-butylene-styrene-copolymer can be used.

The core-member hub 64 comprises a front portion rotatably attached to the second main-tube-hub member 57b and a rear portion provided with an opening 62 communicating with the lumen 58. The opening 62 serves as the dilatation liquid injection port. For the material of the core-member hub 64, thermoplastic resins such as polycarbonate, polyamide, polysulfone, polyallylate and methacrylate-butylene-styrene-copolymer can be used.

The core-member hub 64 has a bore formed through its entire length. The proximal end of the resilient core member 54 is situated around the middle of the bore and secured to the core-member hub 64. Connected to the core-member hub 64 is a tubular member 74 which extends frontward through the inside of the second main-tub-hub member 57b and the sealing ring member 72 up to the inside of the first main-tub-hub member 57a. When the second main-tube-hub members 57b is driven into the first main-tube-hub members 57a, the sealing ring member 72 is pressed between the two main-tube-hub members 57a and 57b and deforms to press against the tubular member 72. The sealing ring member 72 thus holds firmly the tubular member 72 as well as it seals liquid-tight the first and second main-tube-hub members 57a and 57b, the tubular member 74 and the first main-tube-hub member 57a, and the tubular member 74 and the second main-tube-hub member 57b. When the second main-tube-hub members 57b is loosened, the tubular member 74 is released.

A practical sample of the blood vessel dilator with the construction as shown in FIGS. 8 to 13 is described below.

For the resilient core member 54, a metal wire of high-tensile-strength stainless spring steel formed in a single solid and having the following measurements:
Overall length: 1250 mm
Major proximal portion 54e
Diameter: 0.35 mm
Length: 950 mm
First middle portion 54d
Diameter: 0.20 mm
Length: 150 mm
Second middle portion 54c
Diameter: 0.15 mm
Length: 100 mm
Third middle portion 54b
Diameter: 0.12 mm
Length: 30 mm
Distal end portion 54a
Cross section (flat): 0.025×0.075 mm,
length: 20 mm
was used.

For the main tube 52, a plastic tube of polyethylene (length: 1350 mm, diameter: 0.75 mm, inside diameter: 0.6 mm) was used.

For the distal-end tube 53, a plastic tube of polyimide (length: 130 mm, outside diameter: 0.225 mm, inside diameter: 0.175 mm) was used. The marker 61 was formed by winding Pt wire (0.0875 mm in diameter) at a position 15 mm to the proximal side from the front end of the distal-end tube. The maker was 0.35 mm in outside diameter and 1 mm in length.

For the dilatation element 56, a dilatation element of polyester copolymer (outside diameter of cylindrical portion when inflated: 3.0 mm, length of cylindrical portion when inflated: 20 mm, overall length: 30 mm, outside diameter of proximal portion connecting to the main tube: 0.75 mm, outside diameter of distal portion connecting to the distal-end tube: 0.225 mm) was used.

For the reinforcing tube 80, a tube of ethylene-vinyl acetate crosslinked copolymer (outside diameter: 1.5 mm, length: 130 mm) was used.

For the first main-tube-hub member 57a, one with the following measurements and the construction shown in FIG. 13 was formed of polycarbonate.
Overall length: 65 mm
Outside diameter: 16 mm
Inside diameter: 2 mm
Inner cylindrical projection 57c:
Length: 15 mm
Outside diameter: 5 mm
Outer cylindrical projection 57e:
Length: 15 mm
Inside diameter of threaded portion: 10 mm
Inside diameter of portion without thread: 8 mm
Difference of length of inner and outer cylindrical projections: 15 mm For the second main-tube-hub member 57b, one with the following measurements was formed of polycarbonate.
Overall length: 25 mm
Outside diameter: 16 mm
Inside diameter: 2 mm
Cylindrical projection threaded in outside surface 57d:
Length: 10 mm
Inside diameter: 5 mm
Outside diameter: 10 mm
Rear portion with a larger diameter:
Length: 5 mm
Outside diameter: 19 mm For the sealing ring member 72, a ring of silicone rubber (inside diameter: 2 mm, outside diameter: 5 mm) was used.

For the core-member hub 64, one with the following measurements was formed of polycarbonate.
Overall length: 50 mm
Front portion:
Length: 35 mm
Outside diameter: 23 mm
Inside diameter of front opening: 2 mm
Inside diameter of recess receiving rear portion of main-tube hub: 20 mm
Diameter of inside bore: 2 mm For the insert 65, a ring having two holes(inside diameter: 0.225 mm, outside diameter: 0.6 mm, length: 3 mm) was used. This insert was put in between the main tube 52 and the distal end tube 53 at position 100 mm to the distal side from the rear end of the distal-end tube 53.

For the tubular member 71, a stainless steel pipe (outside diameter: 2 mm, length: 60 mm) was used.

The tubular member 71 was connected to the resilient-core-member hub 64. Then the second main-tube-hub member 75 was connected to them, the sealing ring member 72 was put in the second main-tube-hub member 75, the proximal end of the resilient core member 54 was secured to the core-member hub 64, and silicone oil was applied over the surface of the second middle portion 54c of the resilient core member 54.

The proximal end of the main tube 52 was connected to the first main-tube-hub member 57a with a reinforcing tube put in between them. Next, the resilient core member 54 was passed through the inside of the main tube 52 and the distal-end tube 53.

For the leading guide 55, a spiral spring (outside diameter: 0.35 mm, length: 20 mm) was formed of a Pt wire (diameter: 0.08 mm) and attached to the distal end portion of the resilient core member 54 protruding out of the front end of the distal-end tube 53. The spring and the resilient core member 54 were bonded by brazing.

Finally, the dilatation element 56 was attached to the tubes by connecting its front end portion to the front end portion of the distal-end tube 53 and its rear end portion to the distal end portion of the main tube 52.

In this dilator, the length of the distal-end tube 53 protruding out of the distal end of the main tube 52 was 30 mm. The resilient core member 54 can be turned by turning the core-member hub 64. When injecting an X-ray contrast media from the opening 62 and inflating the dilatation element 56, there was no leak of the X-ray contrast media.

Second practical sample of the blood vessel dilator with the construction as shown in FIGS. 8 to 13 is described below.

The blood vessel dilator of second sample was made in the similar manner to the above first sample but using the following main tube and dilatation element.

For the main tube 52 , a plastic tube of a blend of polypropylene and polybuten has a distal portion and a proximal portion (over length: 1350 mm, outside diameter of proximal portion: 0.75 mm, inside diameter of proximal portion: 0.6 mm, length of proximal portion: 1100 mm, outside diameter of distal portion: 0.65 mm, inside diameter of distal portion: 0.5 mm, length of distal portion: 250 mm) was used.

For the dilatation element 56, a dilatation element of polyester copolymer (outside diameter of cylindrical portion when inflated: 3.0 mm, length of cylindrical portion when inflated: 20 mm, overall length: 30 mm, inside diameter of proximal portion connecting to the main tube: 0.65 mm, outside diameter of distal portion connecting to the distal-end tube: 0.225 mm) was used.

Finally, the dilatation element 56 was attached to the tubes by connecting its front end portion to the front end portion of the distal-end tube 53 and its rear end portion to the distal end portion of the main tube 52.

In this second sample dilator, the length of the distal-end tube 53 protruding out of the distal end of the main tube 52 was 30 mm. The resilient core member 54 can be turned by turning the core-member hub 64. When injecting an X-ray contrast media from the opening 62 and inflating the dilatation element 56, there was no leak of the X-ray contrast media.

Third practical sample of the blood vessel dilator with the construction as shown in FIGS. 8 to 13 is described below.

For the resilient core member 54, a metal wire of high-tensile-strength stainless spring steel formed in a single solid and having the following measurements:
Overall length: 1250 mm
Major proximal portion 54e
Diameter: 0.35 mm
Length: 950 mm
First middle portion 54d
Diameter: 0.2 mm
Length: 150 mm
Second middle portion 54c
Diameter: 0.15 mm
Length: 100 mm
Third middle portion 54b
Diameter: 0.12 mm
Length: 30 mm
Distal end portion 54a
Cross section (flat): 0.025×0.075 mm
length: 20 mm
was used.

For the main tube 52, a composite tube made by connecting a metal tube of super-elastic Ni-Ti alloy (length: 1100 mm, outside diameter: 0.75 m, inside diameter: 0.55 mm) for the proximal portion and a plastic tube of a blend of polypropylene and polybutene (length: 250 cm, outside diameter: 0.75 m, inside diameter: 0.65 mm) for the distal portion was used.

For the distal-end tube 53, a plastic tube of palmed (length: 130 mm, outside diameter: 0.225 mm, inside diameter: 0.175 mm) was used.

The marker 61 was formed by winding a Pt-Ir ally wire (0.0875 mm in diameter) at a position 15 mm to the proximal side from the front end of this distal-end tube. The maker was 0.35 mm in outside diameter and 1 mm in length.

For the dilatation element 56, a dilatation element of polyphenylenesulfide (outside diameter of cylindrical portion when inflated: 3 mm, length of cylindrical portion when inflated: 20 mm, overall length: 30 mm) was used.

For the reinforcing tube 80, a tube of ethylene-vinyl acetate crosslinked copolymer (outside diameter: 1.5 mm, length: 130 mm) was used.

For the first main-tube-hub member 57a, one with the following measurements and the construction as shown in FIG. 13 was formed of polycarbonate.
Overall length: 65 mm
Outside diameter: 16 mm
Inside diameter: 2 mm
Inner cylindrical projection 57c:
Length: 15 mm
Outside diameter: 5 mm
Outer cylindrical projection 57e:
Length: 15 mm
Inside diameter of threaded portion: 10 mm
Inside diameter of portion without thread: 12 mm
Difference of length of inner and outer cylindrical projections: 15 mm For the second main-tube-hub member 57b, one with the following measurements was formed of polycarbonate.
Overall length: 25 mm
Outside diameter: 16 mm
Inside diameter: 2 mm
Cylindrical projection threaded in outside surface 57d:
Length: 10 mm
Inside diameter: 5 mm
Outside diameter: 10 mm
Rear portion with a larger diameter:
Length: 5 mm
Outside diameter: 19 mm For the sealing ring member 72, a ring of silicone rubber (inside diameter: 2 mm, outside diameter: 5 cm) was used.

For the core-member hub 64, one with the following measurements was formed of polycarbonate.
Overall length: 50 mm
Front portion:
Length: 35 mm
Outside diameter: 23 mm
Inside diameter of front opening: 2 mm
Inside diameter of recess receiving rear portion of main-tube hub: 20 mm
Diameter of inside bore: 2 mm For the insert 65, a ring insert having two bores (inside diameter: 0.225 mm, outside diameter: 0.6 mm, length: 3 mm) was used. This insert was put in between the main tube 52 and the distal-end tube 53 at position 100 mm to the distal side from the rear end of the distal-end tube 53.

For the tubular member 71, a stainless steel pipe (outside diameter: 2 mm, length: 60 mm) was used. The tubular member 71 was connected to the resilient-core-member hub 64. Then the second main-tube-hub member was connected to them, the sealing ring member 72 was put in the second main-tube-hub member 75, the proximal end of the resilient core member 54 was secured to the core-member hub 64, and silicone oil was applied over the surface of the second middle portion 54c of the resilient core member 54.

The proximal end of the main tube 52 was connected to the first main-tube-hub member 57a with a reinforcing tube put in between them. Next, the resilient core member 54 was passed through the inside of the main tube 52 and the distal-end tube 53.

For the leading guide 55, a spiral spring (outside diameter: 0.35 mm, length: 20 mm) was formed of a Pt-It wire (diameter: 0.08 mm) and attached to the distal end portion of the resilient core member 54 protruding out of the front end of the distal-end tube 53. The spring and the resilient core member 54 were bonded by brazing.

Finally, the dilatation element 56 was attached to the tubes by connecting its front end portion to the front end portion of the distal-end tube 53 and its rear end portion to the distal end portion of the main tube 52.

In this dilator, the length of the distal-end tube 53 protruding out of the distal end of the main tube 52 was 30 mm. The resilient core member 54 can be turned by turning the core-member hub 64. When injecting an X-ray contrast media from the opening 62 and inflating the dilatation element 56, there was no leak of the X-ray contrast media.

The injection of the X-ray contrast media was easier in the blood vessel dilator of the third sample than in that of the first sample.

The blood vessel dilator of the present invention comprises a main tube having a lumen; a distal-end tube put in the distal end portion of the main tube with its front end portion protruding out of the distal end of the main tube; a dilatation element with its front end portion connected to the front end portion of the distal-end tube and its rear end portion to the distal end portion of the main tube and inflatable and contractible or foldable when deflated; a resilient core member put through the inside of the main tube and distal-end tube; a leading guide provided at the distal end portion of the resilient core member; a main-tube hub connected to the proximal end of the main tube; a core-member hub connected to the proximal end of the resilient core member and secured to the main-tube hub turnably with respect to the main tube; and an opening communicating with the lumen in the main tube and serving as a port: and further the distal-end tube being connected to the distal end of the main tube without blocking the communication of the lumen in the main tube and the inside of the dilatation element, and the distal-end tube having a contact portion whose an inside diameter is substantially equal to or slightly larger than the diameter of the resilient core member partially or over its entire length so as to support the resilient core member turnably and liquid-tight.

The another blood vessel dilator of the present invention comprises a main tube having a lumen; a distal-end tube put in the distal end portion of the main tube with its front end portion protruding out of the distal end of the main tube; a dilatation element with its front end portion connected to the front end portion of the distal-end tube and its rear end portion to the distal end portion of the main tube and inflatable and contractible or foldable when deflated; a resilient core member put through the inside of the main tube and distal-end tube; a leading guide provided at the distal end portion of the resilient core member; a main-tube hub connected to the proximal end of the main tube and having an opening communicating with the lumen inside the main tube and serving as a port; and a core-member hub connected to the proximal end of the resilient core member and secured to the main-tube hub turnably: and further the distal-end tube being connected to the distal end of the main tube without blocking the communication of the lumen in the main tube and the inside of the dilatation element, and the distal-end tube having a contact portion whose an inside diameter is so formed substantially equal to or slightly larger than the diameter of the resilient core member partially or over its entire length so as to support the resilient core member turnably and liquid-tight.

The another blood vessel dilator of the present invention comprises a main tube having a smaller-diameter distal end portion and a larger-diameter proximal major portion; a dilatation element with its front end portion connected to the front end portion of the main tube with a smaller diameter and its rear end portion to the major portion of the main tube with a large diameter; a resilient core member put through the inside of the main tube and distal-end tube; a leading guide provided at the distal end portion of the resilient core member; a lumen formed between the proximal major portion of the main tube and the resilient core member; openings provided in the distal end of the proximal major portion of the main tube for communicating the lumen and the inside of the dilatation element with each other; an opening communicating with the lumen in the main tube and serving as a port; a main-tube hub connected to the proximal end of the main tube and having a bore communicating with the lumen inside the main tube; and a core-member hub connected to the proximal end of the resilient core member, secured to the main-tube hub turnably: and further said smaller-diameter distal end portion of the main tube has a substantially equal to or slightly larger diameter than the diameter of the resilient core member.

Therefore, this blood vessel dilator of the present invention has the following advantages.

The resilient core member can be turned freely with respect to the main tube and distal-end tube, which increases the manipulatability of the leading guide and thereby makes easier the insertion of the dilatation element into an aimed lesion in a blood vessel.

The dilatation element does not turn if the leading guide is turned, and consequently occurrence of a twist in the dilatation element can be prevented.

The rear end of the distal-end tube is not extended up to the proximal end of the main tube, leaving a larger cross section for the lumen in the main tube. As the result, injection of a dilatation liquid and hence treatment of stenosis in blood vessels is made easier.

We claim:
1. A blood vessel dilator comprising:
   a main tube having a lumen;
   a distal-end tube put in a distal end portion of the main tube with a front end portion of the distal-end tube protruding out of the distal end of the main tube;
   a dilatation element with a front end portion of the dilatation element connected to a front end portion of the distal-end tube and a rear end portion of the dilatation element connected to the distal end portion of the main tube, and being inflatable and contractible or foldable when deflated;
   a resilient core member put through the lumen of the main tube and an inside of the distal-end tube;
   a leading guide provided at a distal end portion of the resilient core member;
   a main-tube hub connected to a proximal end of the main tube;
   a core-member hub connected to a proximal end of the resilient core member and secured to the main-tube hub turnably with respect to the main tube;
   an opening communicating with the lumen in the main tube and serving as a port; and
   the distal-end tube being connected to the distal end of the main tube without blocking the communica- tion of the lumen in the main tube and an inside of the dilatation element, and the distal-end tube having a contact portion whose inside diameter is substantially equal to or slightly larger than the diameter of the resilient core member partially or over an entire length of the resilient core member so as to support the resilient core member turnably and liquid-tight;

wherein an inside diameter of the rear end portion of said distal-end tube is smaller than an inside diameter of the front end portion of said distal-end tube to form said contact portion in the front end portion.

2. A blood vessel dilator as defined in claim 1, in which said main tube has a length two times or more greater than that of said distal-end tube.

3. A blood vessel dilator as defined in claim 1, in which said resilient core member has a proximal portion with a high resilience and a flexible distal portion.

4. A blood vessel dilator as defined in claim 1, in which said core-member hub comprises a knob-like portion serving as a means of turning said resilient core member and restricting the move of said resilient core member in the direction of an axis of the resilient core member.

5. A blood vessel dilator as defined in claim 1, in which said opening communicating with said lumen of the main tube and serving as a port is provided in said core-member hub.

6. A blood vessel dilator as defined in claim 1, in which said main-tube hub and said core-member hub are connected turnably and liquid-tight.

7. A blood vessel dilator as defined in claim 1, in which a portion of said resilient core member situated in said distal-end tube has continuously or stepwise decreasing diameters to the distal end.

8. A blood vessel dilator as defined in claim 1, in which a lubricant is applied to said contact portion of said distal-end tube.

9. A blood vessel dilator as defined in claim 1, in which said main tube includes a metal tube for the proximal portion which is longer than half the total length of said main tube and a flexible plastic tube connected to the metal tube to form said distal portion and to make it flexible.

10. A blood vessel dilator comprising:
a main tube having a lumen;
a distal-end tube put in a distal end portion of the main tube with a front end portion of the distal-end tube protruding out of a distal end of the main tube;
a dilatation element with a front end portion of the dilatation element connected to a front end portion of the distal-end tube and a rear end portion of the dilatation element connected to the distal end portion of the main tube, and being inflatable and contractible or foldable when deflated;
a resilient core member put through the lumen of the main tube and an inside of the distal-end tube;
a leading guide provided at a distal end portion of the resilient core member;
a main-tube hub connected to a proximal end of the main tube and having an opening communicating with the lumen inside the main tube and serving as a port;
a core-member hub connected to the proximal end of the resilient core member and secured to the main-tube hub turnably; and the distal-end tube being connected to the distal end of the main tube without blocking the communication of the lumen in the main tube and an inside of the dilatation element, and the distal-end tube having a contact portion whose inside diameter is formed substantially equal to or slightly larger than the diameter of the resilient core member partially or over an entire length of the resilient core member so as to support the resilient core member turnably and liquid-tight;

wherein an inside diameter of the rear end portion of said distal-end tube is smaller than an inside diameter of the front end portion of said distal-end tube to form said contact portion in the front end portion.

11. A blood vessel dilator as defined in claim 10, in which said main tube has a length two times or more greater than that of said distal-end tube.

12. A blood vessel dilator as defined in claim 10, in which said resilient core member has a proximal portion with a high resilience and a flexible distal portion.

13. A blood vessel dilator as defined in claim 10, in which said core-member hub comprises a knob-like portion serving as a means of turning said resilient core member and restricting the move of said resilient core member in the direction of an axis of the resilient core member.

14. A blood vessel dilator as defined in claim 10, in which said main-tube hub and said core-member hub are connected turnably and liquid-tight.

15. A blood vessel dilator as defined in claim 10, in which a lubricant is applied to said contact portion of said distal-end tub.

16. A blood vessel dilator as defined in claim 10, in which said main tube includes a metal tube for the proximal portion which is longer than half the total length of said main tube and a flexible plastic tube connected to the metal tube to form said distal portion and to make it flexible.

17. A blood vessel dilator comprising
a main tube having a smaller-diameter distal end portion and a larger-diameter proximal major portion;
a dilatation element with a front end portion of the dilatation element connected to a front end portion of the main tube with a smaller diameter and a rear end portion of the dilatation element to the major portion of the main tube with a large diameter;
a resilient core member put through an inside of the main tube and an inside of the distal-end tube;
a leading guide provided at a distal end portion of the resilient core member;
a lumen formed between a proximal major portion the main tube and the resilient core member;
a bore provided in the distal end of the proximal major portion of the main tube for communicating the lumen and an inside of the dilatation element with each other;
an opening communicating with the lumen formed between the proximal major portion of the main tube and the resilient core member;
a main-tube hub connected to the proximal end of the main tube and having a bore communicating with the lumen inside the main tube;
a core-member hub connected to the proximal end of the resilient core member, secured to the main-tube hub turnably: and
said smaller-diameter distal end portion of the main tube has a substantially equal to or slightly larger diameter than the diameter of the resilient core member so as to support the resilient core member turnably and liquid-tight.

18. A blood vessel dilator as defined in claim 17, in which said resilient core member has a proximal portion with a high resilience and a flexible distal portion.

19. A blood vessel dilator as defined in claim 19, in which said core-member hub comprises a knob-like portion serving as a means of turning said resilient core member and restricting the move of said resilient core member in the direction of its length.

20. A blood vessel dilator as defined in claim 17, in which said opening communicating with said lumen and serving as a port is provided in said main-tube hub.

21. A blood vessel dilator as defined in claim 17, in which said main-tube hub and said core-member hub are connected turnably and liquid-tight.

22. A blood vessel dilator as defined in claim 17, in which a lubricant is applied to said smaller-diameter distal end portion of the main tube and the resilient core member.

23. A blood vessel dilator as defined in claim 17, in which said main tube includes a metal tube for the proximal portion which is longer than half the total length of said main tube and a flexible plastic tube connected to the metal tube to form said distal portion and to make it flexible.

24. A blood vessel dilator comprising:
a main tube having a lumen;
a distal-end tube put in a distal end portion of the main tube with a front end portion of the distal-end tube protruding out of the distal end of the main tube;
a dilatation element with a front end portion of the dilatation element connected to a front end portion of the distal-end tube and a rear end portion of the dilatation element connected to the distal end portion of the main tube, and being inflatable and contractible or foldable when deflated;
a resilient core member put through the lumen of the main tube and an inside of the distal-end tube, and arranged so as to be freely turnable with respect to the main tube and the distal-end tube;
a leading guide provided at a distal end portion of the resilient core member;
a main-tube hub connected to a proximal end of the main tube;
a core-member hub connected to a proximal end of the resilient core member and secured to the main-tube hub turnably with respect to the main tube;
an opening communicating with the lumen in the main tube and serving as a port;
an inside of the dilatation element being in communication with the lumen in the main tube; and
the distal-end tube having a contact portion which contacts a distal portion of the resilient core-member;
wherein an inside diameter of the contact portion of the distal-end tube is substantially equal to or slightly larger than the diameter of the resilient core member over at least a part of the length of the resilient core member.

25. A blood vessel dilator as defined in claim 24, in which said main tube has a length at least two times greater than that of said distal-end tube.

26. A blood vessel dilator as defined in claim 24, in which said resilient core member has a proximal portion with a high resilience and a flexible distal portion.

27. A blood vessel dilator as defined in claim 24, in which an inside diameter of the rear end portion of said distal-end tube is smaller than an inside diameter of the front end portion of said distal-end tube to form said contact portion in the front end portion.

28. A blood vessel dilator as defined in claim 24, in which said main tube includes a metal tube for the proximal portion which is longer than half the total length of said main tube and a flexible plastic tube connected to the metal tube to form said distal portion and to make it flexible.

29. A blood vessel dilator as defined in claim 24, in which said core-member hub comprises a knob-like portion serving as a means of turning said resilient core member and restricting movement of said resilient core member in the axial direction thereof.

30. A blood vessel dilator as defined in claim 24, in which said opening communicating with said lumen of the main tube and serving as a port is provided in said core-member hub.

31. A blood vessel dilator as defined in claim 24, in which said main tube hub and said core-member hub are connected turnably and liquid-tight.

32. A blood vessel dilator as defined in claim 24, in which a portion of said resilient core member situated in said distal-end tube has continuously or stepwise decreasing diameters to the distal end.

33. A blood vessel dilator as defined in claim 24, in which a lubricant is applied to said contact portion of said distal-end tube.

34. A blood vessel dilator comprising:
a main tube having a lumen;
a distal-end tube put in a distal end portion of the main tube with a front end portion of the distal-end tube protruding out of the distal end of the main tube;
a dilatation element with a front end portion of the dilatation element connected to a front end portion of the distal-end tube and a rear end portion of the dilatation element connected to the distal end portion of the main tube, and being inflatable and contractible or foldable when deflated;
a resilient core member put through the lumen of the main tube and an inside of the distal-end tube;
a leading guide provided at a distal end portion of the resilient core member;
a main-tube hub connected to a proximal end of the main tube;
a core-member hub connected to a proximal end of the resilient core member and secured to the main-tube hub turnably with respect to the main tube;
an opening communicating with the lumen in the main tube and serving as a port; and
the distal-end tube being connected to the distal end of the main tube without blocking the communication of the lumen in the main tube and an inside of the dilatation element, and the distal-end tube having a contact portion whose inside diameter is substantially equal to or slightly larger than the diameter of the resilient core member partially or over an entire length of the resilient core member so as to support the resilient core member turnably and liquid-tight;
wherein said main tube includes a metal tube for the proximal portion which is longer than half the total length of said main tube, and a flexible plastic tube connected to the metal tube to form said distal end portion and to make it flexible.

35. A blood vessel dilator comprising:
a main tube having a lumen;
a distal-end tube put in a distal end portion of the main tube with a front end portion of the distal-end tube protruding out of a distal end of the main tube;
a dilatation element with a front end portion of the dilatation element connected to a front end portion of the distal-end tube and a rear end portion of the dilatation element connected to the distal end portion of the main tube, and being inflatable and contractible or foldable when deflated;
a resilient core member put through the lumen of the main tube and an inside of the distal-end tube;
a leading guide provided at a distal end portion of the resilient core member;
a main-tube hub connected to a proximal end of the main tube and having an opening communicating with the lumen inside the main tube and serving as a port;
a core-member hub connected to the proximal end of the resilient core member and secured to the main-tube hub turnably; and
the distal-end tube being connected to the distal end of the main tube without blocking the communication of the lumen in the main tube and an inside of the dilatation element, and the distal-end tube having a contact portion whose inside diameter is formed substantially equal to or slightly larger than the diameter of the resilient core member partially or over an entire length of the resilient core member so as to support the resilient core member turnably and liquid-tight;
wherein said main tube includes a metal tube for the proximal portion which is longer than half the total length of said main tube, and a flexible plastic tube connected to the metal tube to form said distal end portion and to make it flexible.

36. A blood vessel dilator comprising:
a main tube having a lumen;
a distal-end tube put in a distal end portion of the main tube with a front end portion of the distal-end tube protruding out of the distal end of the main tube;
a dilatation element with a front end portion of the dilatation element connected to a front end portion of the distal-end tube and a rear end portion of the dilatation element connected to the distal end portion of the main tube, and being inflatable and contractible or foldable when deflated;
a resilient core member put through the lumen of the main tube and an inside of the distal-end tube, and arranged so as to be freely turnable with respect to the main tube and the distal-end tube;
a leading guide provided at a distal end portion of the resilient core member;
a main-tube hub connected to a proximal end of the main tube;
a core-member hub connected to a proximal end of the resilient core member and secured to the main-tube hub turnably with respect to the main tube;
an opening communicating with the lumen in the main tube and serving as a port;
an inside of the dilatation element being in communication with the lumen in the main tube; and
the distal-end tube having a contact portion which contacts a distal portion of the resilient core-member;
wherein an inside diameter of the rear end portion of said distal-end tube is smaller than an inside diameter of the front end portion of said distal-end tube to form said contact portion in the front end portion.

* * * * *

UNITED STATES PATENT AND TRADEMARK OFFICE
CERTIFICATE OF CORRECTION

PATENT NO. : 5,403,339
DATED : April 4, 1995
INVENTOR(S) : NOBUYOSHI et al.

It is certified that error appears in the above-indentified patent and that said Letters Patent is hereby corrected as shown below:

Title page, Item [56] References Cited, under

"U.S.PATENT DOCUMENTS"

delete the following references:

```
"3,703,899  11/1972  Calinog..................604/170"
"4,362,150  12/1982  Lombardi, Jr. et al......604/99"
"4,723,936   2/1988  Buchbinder et al.........604/95"
"4,917,666   4/1990  Solar et al..............604/95"
"4,931,036   6/1990  Kani et al...............604/99"
"4,932,959   6/1990  Horzewski et al..........604/96"
"4,998,923   3/1991  Samson et al.............604/95"
```

Column 1, line 29, "4,77,778" should be --4,771,778--.

Column 12, line 59, "II-II" should be --III-III--.

Column 13, line 55, "ore" should be --more--.

Column 20, line 55, before "was" insert --75--.

Column 25, line 7 (claim 19),
"claim 19" should be --claim 17--

Signed and Sealed this

Seventh Day of October, 1997

Attest:

BRUCE LEHMAN

Attesting Officer

Commissioner of Patents and Trademarks